(12) United States Patent
Miller et al.

(10) Patent No.: US 7,511,035 B2
(45) Date of Patent: Mar. 31, 2009

(54) ANTIBACTERIAL AGENTS

(75) Inventors: William Henry Miller, Collegeville, PA (US); Meagan B. Rouse, Collegeville, PA (US); Mark Andrew Seefeld, Collegeville, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/814,611

(22) PCT Filed: Jan. 24, 2006

(86) PCT No.: PCT/US2006/002617

§ 371 (c)(1), (2), (4) Date: Jul. 24, 2007

(87) PCT Pub. No.: WO2006/081289

PCT Pub. Date: Aug. 3, 2006

(65) Prior Publication Data

US 2008/0139539 A1  Jun. 12, 2008

Related U.S. Application Data

(60) Provisional application No. 60/646,813, filed on Jan. 25, 2005.

(51) Int. Cl.
*C07D 498/04* (2006.01)
*C07D 513/04* (2006.01)
*A61K 31/542* (2006.01)
*A61K 31/436* (2006.01)

(52) U.S. Cl. ............... 514/224.2; 544/48; 544/105; 544/362; 514/230.5; 514/253.04

(58) Field of Classification Search ............ 544/48, 544/105, 362; 514/224.2, 230.5, 253.04
See application file for complete search history.

(56) References Cited

U.S. PATENT DOCUMENTS

| | | | |
|---|---|---|---|
| 5,534,537 A | 7/1996 | Ciccarone et al. | 514/397 |
| 6,090,807 A | 7/2000 | Hellendahl et al. | 514/252 |
| 6,214,822 B1 | 4/2001 | Treiber et al. | 514/218 |
| 6,329,405 B1 | 12/2001 | Kurata et al. | 514/357 |
| 6,403,610 B1 | 6/2002 | Malleron et al. | 514/314 |
| 6,602,882 B1 | 8/2003 | Davies et al. | 514/300 |
| 6,602,884 B2 | 8/2003 | Bacque et al. | 514/314 |
| 6,603,005 B2 | 8/2003 | Baque et al. | 546/176 |
| 6,642,288 B1 | 11/2003 | Hulskotte | 524/100 |
| 6,727,239 B1 | 4/2004 | Chabrier de Lassauniere et al. | 514/184 |
| 6,747,024 B1 | 6/2004 | Auvin et al. | 514/224.8 |
| 6,841,562 B2 | 1/2005 | Bacque et al. | 514/314 |
| 6,911,442 B1 | 6/2005 | Davies et al. | 514/230.5 |
| 6,962,917 B2 | 11/2005 | Davies et al. | 514/264.1 |
| 6,989,447 B2 | 1/2006 | Markwell et al. | 546/152 |
| 6,995,144 B2 | 2/2006 | Ozaki et al. | 514/30.5 |
| 7,001,913 B1 | 2/2006 | Davies et al. | 514/300 |
| 7,074,801 B1 | 7/2006 | Yoshida et al. | |
| 7,109,213 B2 | 9/2006 | Daines et al. | 514/312 |
| 7,141,564 B2 | 11/2006 | Brooks et al. | 514/224.2 |
| 7,186,730 B2 | 3/2007 | Dartois et al. | 514/300 |
| 7,205,408 B2 | 4/2007 | Davies et al. | 546/153 |
| 7,312,212 B2 | 12/2007 | Daines et al. | 514/228.2 |
| 2004/0087619 A1 | 5/2004 | Bacque et al. | 514/314 |
| 2006/0014749 A1 | 1/2006 | Davies et al. | 514/249 |
| 2006/0058287 A1 | 3/2006 | Axten et al. | 514/224.2 |
| 2006/0189601 A1 | 8/2006 | Hennessy et al. | 514/222.8 |
| 2006/0189604 A1 | 8/2006 | Axten et al. | 514/224.2 |
| 2007/0135422 A1 | 6/2007 | Brooks et al. | 514/224.8 |

FOREIGN PATENT DOCUMENTS

| | | |
|---|---|---|
| EP | 0 410 762 A1 | 1/1991 |
| JP | 08337569 | 12/1996 |
| JP | 2001354563 | 12/2001 |
| WO | WO 96/30015 | 10/1996 |
| WO | WO 99/37635 | 7/1999 |
| WO | WO 99/62904 | 12/1999 |
| WO | WO 00/21948 | 4/2000 |
| WO | WO 00/21952 | 4/2000 |
| WO | WO 00/35889 | 6/2000 |
| WO | WO 00/43383 | 7/2000 |
| WO | WO 00/78748 A1 | 12/2000 |
| WO | WO 01/07432 A2 | 2/2001 |
| WO | WO 01/07433 A2 | 2/2001 |
| WO | WO 01/39759 | 6/2001 |
| WO | WO 02/08224 A1 | 1/2002 |
| WO | WO 02/24684 A1 | 3/2002 |
| WO | WO 02/42272 | 5/2002 |
| WO | WO 02/42273 | 5/2002 |
| WO | WO 02/50040 A1 | 6/2002 |
| WO | WO 02/50061 A1 | 6/2002 |

(Continued)

OTHER PUBLICATIONS

Snyder et al., PubMed Abstract (J. Med. Liban 48(4): 208-214, Jul.-Aug. 2000.*

(Continued)

*Primary Examiner*—Kahsay T Habte
(74) *Attorney, Agent, or Firm*—Loretta J. Sauermelch; Charles M. Kinzig

(57) ABSTRACT

Naphthyridine and quinoline derivatives useful in the treatment of bacterial infections in mammals, particularly humans, are disclosed herein.

20 Claims, No Drawings

FOREIGN PATENT DOCUMENTS

| | | |
|---|---|---|
| WO | WO 02/051396 | 7/2002 |
| WO | WO 02/056882 A1 | 7/2002 |
| WO | WO 02/057236 | 7/2002 |
| WO | WO 02/062766 | 8/2002 |
| WO | WO 02/070471 | 9/2002 |
| WO | WO 02/096907 A1 | 12/2002 |
| WO | WO 03/010138 A2 | 2/2003 |
| WO | WO 03/064421 A1 | 8/2003 |
| WO | WO 03/064431 A2 | 8/2003 |
| WO | WO 03/087098 A1 | 10/2003 |
| WO | WO 2004/002490 A2 | 1/2004 |
| WO | WO 2004/002992 A1 | 1/2004 |
| WO | WO 2004/087145 A2 | 10/2004 |
| WO | WO 2004/096982 A2 | 11/2004 |
| WO | WO 2005/019215 | 3/2005 |
| WO | WO 2006/081179 A1 | 8/2006 |

OTHER PUBLICATIONS

U.S. Appl. No. 11/814,609, filed Jan. 24, 2006, Miller et al.

Abstract No. 97-103680/10 (JP 08337569-A), Derwent Information Ltd., New amide derivs. e.g. 5-(4-acetamide-4-phenyl-piperidin-1-yl)-N-(2-adamantyl)-2-(3,4-dichlorophenyl)pentanamide—are analgesics with activity comparable to that of morphine.

Abstract No. 2000-431551/37 (WO 200035889-A1), Derwent Information Ltd., Ileal bile acid transporter inhibitor containing new of known (thi)oxo-heterocyclyl benzylamine compounds, used for treating hyperlipidemia and arteriosclerosis.

Abstract No. 2002-247412/30 (JP 2001354563-A), Derwent Information Ltd., Medicine comprising substituted benzylamine, having inhibitory activity of ileo type bile acid transporter, useful in the treatment of hyperlipemia or arteriosclerosis.

Abstract No. 2002-508878/54 (WO 200251396-A1), Derwent Information Ltd., Compositions useful for treating and preventing e.g. hyperlipemia and arteriosclerosis, comprise HMG-CoA reductase inhibitors and cyclobutene derivatives.

* cited by examiner

ANTIBACTERIAL AGENTS

This application is a national stage entry of PCT/US2006/002617, filed Jan. 24, 2006, which claims the benefit of U.S. Provisional Application No. 60/646,813, filed Jan. 25, 2005.

FIELD OF THE INVENTION

This invention relates to novel compounds, compositions containing them, their use as antibacterials, and processes for their preparation.

BACKGROUND OF THE INVENTION

The emergence of pathogens resistant to known antibiotic therapy is becoming a serious global healthcare problem (Chu, et al., (1996) *J. Med. Chem.,* 39: 3853-3874). Thus, there is a need to discover new broad spectrum antibiotics useful in combating multidrug-resistant organisms. Importantly, it has now been discovered that certain compounds have antibacterial activity, and, therefore, may be useful for the treatment of bacterial infections in mammals, particularly in humans. WO0125227, WO0240474, WO0207572, WO04024712, WO04024713, WO9937635, WO0021948, WO0021952, WO0043383, WO0078748, WO0107433, WO0107432, WO0208224, WO0224684, WO0250061, WO0250040, WO0256882, WO0296907, WO03087098, WO03010138, WO03064431, WO03064421, WO04002992, and WO0400249 disclose quinoline and/or naphthyridine derivatives having antibacterial activity.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also processes for the preparation of compounds of formula (I), as well as processes for the preparation of intermediates useful in the synthesis of compounds of formula (I). This invention is also a method of treating bacterial infections in mammals, particularly in humans.

DETAILED DESCRIPTION OF THE INVENTION

In some embodiments, this invention describes a compound of formula (I)

wherein:
Z is CH or N;
R is hydrogen or F;
$W_3$ is CH; C(OH); or N;
$W_1$, $W_2$, $W_4$, and $W_5$ are $CH_2$; or
one of $W_1$, $W_2$, $W_4$, and $W_5$ is C=O and the others are $CH_2$;
A is $CH_2$ or CH(OH);
$R_1$ is 4H-Pyrido[3,2-b][1,4]thiazin-3-oxo-6-yl; 4H-Pyrido[3,2-b][1,4]oxazin-3-oxo-6-yl; or 2,3-Dihydro-[1,4]dioxino[2,3-c]-pyridin-6-yl; or
a pharmaceutically acceptable salt or solvate thereof.

In some embodiments, this invention describes a compound of formula (I) wherein Z is N.

In some embodiments, this invention describes a compound of formula (I) wherein R is F.

In some embodiments, this invention describes a compound of formula (I) wherein $W_3$ is N.

In some embodiments, this invention describes a compound of formula (I) wherein $W_3$ is $CH_2$.

In some embodiments, this invention describes a compound of formula (I) wherein $W_3$ is CH(OH).

In some embodiments, this invention describes a compound according to formula (I) wherein $W_1$, $W_2$, $W_4$, and $W_5$ are $CH_2$.

In some embodiments, this invention describes a compound according to formula (I) wherein one of $W_1$, $W_2$, $W_4$, and $W_5$ is C=O.

In some embodiments, this invention describes a compound of formula (I) wherein the compound is 6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one, 6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one, 6-{[(2-{4-[3-fluoro-6-(methyloxy)-4-quinolinyl]-1-piperazinyl}ethyl)amino]methyl}-2H-pyrido[3,2-b][1,4]thiazin-3(4H)-one, 6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one, 6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]thiazin-3(4H)-one, 6-{[(2-{4-[6-(methyloxy)-1,5-naphthyridin-4-yl]-3-oxo-1-piperazinyl}ethyl)amino]methyl}-2H-pyrido[3,2-b][1,4]oxazin-3(4H)-one, 4-{2-[(2,3-dihydro[1,4]dioxino[2,3-c]pyridin-7-ylmethyl)amino]ethyl}-1-[3-fluoro-6-(methyloxy)-1,5-naphthyridin-4-yl]-2-piperazinone, 6-{[(2-{4-[6-(methyloxy)-1,5-naphthyridin-4-yl]-3-oxo-1-piperazinyl}ethyl)amino]methyl}-2H-pyrido[3,2-b][1,4]thiazin-3(4H)-one, 6-{[(2-{4-[6-(methyloxy)-1,5-naphthyridin-4-yl]-3-oxo-1-piperazinyl}ethyl)amino]methyl}-2H-pyrido[3,2-b][1,4]oxazin-3(4H)-one, 4-{2-[(2,3-dihydro[1,4]dioxino[2,3-c]pyridin-7-ylmethyl)amino]ethyl}-1-[6-(methyloxy)-1,5-naphthyridin-4-yl]-2-piperazinone, 6-{[(2-{4-[6-(methyloxy)-1,5-naphthyridin-4-yl]-2-oxo-1-piperazinyl}ethyl)amino]methyl}-2H-pyrido[3,2-b][1,4]thiazin-3(4H)-one, 1-{2-[(2,3-dihydro[1,4]dioxino[2,3-c]pyridin-7-ylmethyl)amino]ethyl}-4-[6-(methyloxy)-1,5-naphthyridin-4-yl]-2-piperazinone, 6-{[(2-{1-[3-fluoro-6-(methyloxy)-1,5-naphthyridin-4-y]-4-piperidinyl}ethyl)amino]methyl}-2H-pyrido[3,2-b][1,4]thiazin-3(4H)-one, 6-{[(2-{1-[3-fluoro-6-(methyloxy)-1,5-naphthyridin-4-yl]-4-piperidinyl}ethyl)amino]methyl}-2H-pyrido[3,2-b][1,4]oxazin-3(4H)-one, 6-{[(2-{1-[3-fluoro-6-(methyloxy)-4-quinolinyl]-4-piperidinyl}ethyl)amino]methyl}-2H-pyrido

[3,2-b][1,4]thiazin-3(4H)-one, 6-{[(2-{1-[3-fluoro-6-(methyloxy)-4-quinolinyl]-4-piperidinyl}ethyl)amino]methyl}-2H-pyrido[3,2-b][1,4]oxazin-3(4H)-one, 6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one, 6-{[(2-{1-[3-fluoro-6-(methyloxy)-4-quinolinyl]-4-hydroxy-4-piperidinyl}ethyl)amino]methyl}-2H-pyrido[3,2-b][1,4]oxazin-3(4H)-one, or 6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one, or a pharmaceutically acceptable salt or solvate thereof.

In some embodiments, this invention describes a pharmaceutical composition comprising a compound of formula (I) and a pharmaceutically acceptable carrier.

In some embodiments, this invention describes a method of treating bacterial infections in mammals which comprises administering to a mammal in need thereof an effective amount of a compound according to formula (I).

Unless otherwise defined, the term "alkyl" when used alone or when forming part of other groups (such as the 'alkoxy' group) includes substituted or unsubstituted, straight or branched chain alkyl groups containing the specified range of carbon atoms. For example, the term "$(C_{1-6})$alkyl" include methyl, ethyl, propyl, butyl, iso-propyl, sec-butyl, tert-butyl, iso-pentyl, and the like.

The term "alkenyl" means a substituted or unsubstituted alkyl group of the specified range of carbon atoms, wherein one carbon-carbon single bond is replaced by a carbon-carbon double bond. For example, the term "$(C_{2-6})$alkenyl" include ethylene, 1-propene, 2-propene, 1-butene, 2-butene, and isobutene, and the like. Both cis and trans isomers are included.

The term "cycloalkyl" refers to substituted or unsubstituted carbocyclic system of the specified range of carbon atoms, which may contain up to two unsaturated carbon-carbon bonds. For example, the term "$(C_{3-7})$cycloalkyl" include cyclopropyl, cyclobutyl, cyclopentyl, cyclopentenyl, cyclohexyl, cyclohexenyl, and cycloheptyl.

The term "alkoxy" refers to an O-alkyl radical where the alkyl group contains the specified range of carbon atoms and is as defined herein.

The term "acyl" refers to a C(=O)alkyl or a C(=O)aryl radical. In some embodiments, the alkyl group contains 13 or less carbons; in some embodiments 10 or less carbon atoms; in some embodiments 6 or less carbon atoms; and is as otherwise defined. Aryl is as defined herein.

The term "alkylcarbonyl" refers to a $(C_{1-6})$alkyl(C=O)$(C_{1-6})$alkyl group wherein alkyl is as otherwise defined herein.

The term "alkylsulphonyl" refers to a $SO_2$alkyl radical wherein the alkyl group contains the specified range of carbon atoms and is as defined herein.

The term "alkylthio" refers to a Salkyl wherein the alkyl group contains the specified range of carbon atoms and is as defined herein.

The term "aminosulphonyl" refers to a $SO_2N$ radical wherein the nitrogen is substituted as specified.

The term "aminocarbonyl" refers to a carboxamide radical wherein the nitrogen of the amide is substituted as defined.

The term "heterocyclylthio" refers to a S-heterocyclyl radical wherein the heterocyclyl moiety is as defined herein.

The term "heterocyclyloxy" refers to an O-heterocyclyl radical wherein heterocyclyl is as defined herein.

The term "arylthio" refers to an S-aryl radical wherein aryl is as defined herein.

The term "aryloxy" refers to an O-aryl radical wherein aryl is as defined herein.

The term "acylthio" refers to a S-acyl radical wherein acyl is as defined herein.

The term "acyloxy" refers to an O-acyl radical wherein acyl is as defined herein.

The term "alkoxycarbonyl" refers to a $CO_2$alkyl radical wherein the alkyl group contains the specified range of carbon atoms and is as defined herein.

The term "alkenyloxycarbonyl" refers to a $CO_2$alkyl radical wherein the alkenyl group contains the specified range of carbon atoms and is as defined herein.

The term "alkylsulphonyloxy" refers to an O—$SO_2$alkyl radical wherein the alkyl group contains the specified range of carbon atoms and is as defined herein.

The term "arylsulphonyl" refers to a $SO_2$aryl radical wherein aryl is as herein defined.

The term "arylsulphoxide" refers to a SOaryl radical wherein aryl is as defined herein.

Unless otherwise defined, suitable substituents for any alkyl, alkoxy, alkenyl, and cycloalkyl groups includes up to three substituents selected from the group consisting of hydroxy, halogen, nitro, cyano, carboxy, amino, amidino, sulphonamido, unsubstituted $(C_{1-3})$alkoxy, trifluoromethyl, and acyloxy.

Halo or halogen includes fluoro, chloro, bromo and iodo.

The term "haloalkyl" refers to an alkyl radical containing the specified range of carbon atoms and is as otherwise defined herein, which is further substituted with 1-3 halogen atoms.

The term "haloalkoxy" refers to an alkoxy radical of the specified range and as defined herein, which is further substituted with 1-3 halogen atoms.

The term "hydroxyalkyl" refers to an alkyl group as defined herein, further substituted with a hydroxy group.

Unless otherwise defined, the term "heterocyclic" or "heterocyclyl" as used herein includes optionally substituted aromatic and non-aromatic, single and fused, mono- or bicyclic rings suitably containing up to four hetero-atoms in each ring selected from oxygen, nitrogen and sulphur, which rings may be unsubstituted or C-substituted by, for example, up to three groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; hydroxy, $(C_{1-4})$alkyl; $(C_{1-4})$thioalkyl; $(C_{1-4})$alkoxy; nitro; cyano, carboxy; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl.

Each heterocyclic ring suitably has from 3 to 7, preferably 5 or 6, ring atoms. A fused heterocyclic ring system may include carbocyclic rings and need include only one heterocyclic ring.

Compounds within the invention containing a heterocyclyl group may occur in two or more tautomeric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include hydrogen; trifluoromethyl; $(C_{1-4})$alkyl optionally substituted by hydroxy, $(C_{1-4})$alkoxy, $(C_{1-4})$alkylthio, halo or trifluoromethyl; and $(C_{2-4})$alkenyl.

The term "heterocyclylalkyl" refers to a $(C_{1-6})$alkyl radical which bears as a substituent a heterocyclyl group, wherein heterocyclyl and alkyl are as herein defined. The heterocyclyl group maybe joined to a primary, secondary or tertiary carbon of the $(C_{1-6})$alkyl chain.

When used herein the term "aryl", includes optionally substituted phenyl and naphthyl.

Aryl groups may be optionally substituted with up to five, preferably up to three, groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; $(C_{1-4})$hydroxyalkyl; $(C_{1-4})$alkylthio; $(C_{1-4})$alkoxy; nitro; cyano; carboxy; amino or aminocarbonyl optionally substituted by $(C_{1-4})$alkyl; $(C_{1-4})$alkylsulphonyl; $(C_{2-4})$alkenylsulphonyl.

The term "aralkyl" refers to a $(C_{1-6})$alkyl radical which bears as a substituent an aryl group, wherein aryl and alkyl are as herein defined. The aryl group maybe joined to a primary, secondary or tertiary carbon of the $(C_{1-6})$alkyl chain.

This invention also contemplates that some of its structural embodiments maybe present as a solvate. Solvates maybe produced from crystallization from a given solvent or mixture of solvents, inorganic or organic. Solvates may also produced upon contact or exposure to solvent vapors, such as water. This invention includes within its scope stoichiometric and non-stoichiometric solvates including hydrates.

Furthermore, it will be understood that phrases such as "a compound of Formula I or a pharmaceutically acceptable salt, solvate or derivative thereof" are intended to encompass the compound of Formula I, a derivative of formula (I), a pharmaceutically acceptable salt of the compound of formula (I), a solvate of formula (I), or any pharmaceutically acceptable combination of these. Thus by way of non-limiting example used here for illustrative purpose, "a compound of Formula I or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable salts of the above-mentioned compounds of formula (I) include the free base form or their acid addition or quaternary ammonium salts, for example their salts with mineral acids e.g. hydrochloric, hydrobromic, sulphuric, nitric or phosphoric acids, or organic acids, e.g. acetic, fumaric, succinic, maleic, citric, benzoic; p-toluene-sulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives. One of skill in the art will recognize that where compounds of the invention contain multiple basic sites, a compound of the invention maybe present as a salt complexed with more than one equivalent of a corresponding acid or mixture of acids.

Pharmaceutically acceptable derivatives refers to compounds of formula (I) that have been covalently modified with a group that undergoes at least some in vivo cleavage to a compound of formula (I).

Examples of suitable pharmaceutically acceptable in vivo hydrolysable ester-forming groups include those forming esters which break down readily in the human body to leave the parent acid or its salt.

Suitable groups of this type include those of part formulae (i), (ii), (iii), (iv) and (v):

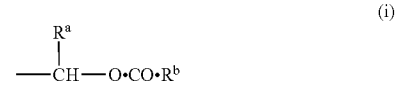

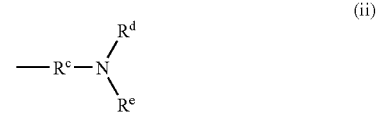

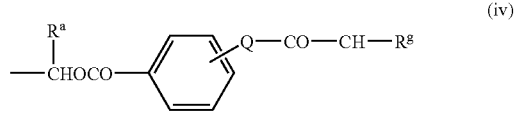

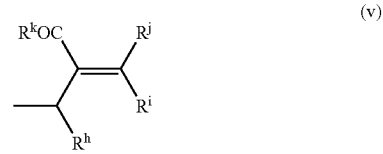

wherein $R^a$ is hydrogen, $(C_{1-6})$ alkyl, $(C_{3-7}$ cycloalkyl, methyl, or phenyl, $R^b$ is $(C_{1-6})$ alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$ cycloalkyl, 1-amino$(C_{1-6})$alkyl, or 1-$(C_{1-6}$ alkyl)amino$(C_{1-6})$ alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$alkoxycarbonyl; and $R^k$ represents $(C_{1-8})$alkyl, $(C_{1-8})$alkoxy, $(C_{1-6})$alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, acetoxyethyl, pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$ alkyl groups, such as ethoxycarbonyloxymethyl, ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-$(C_{1-6})$alkoxycarbonyl)-2-$(C_{2-6})$alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

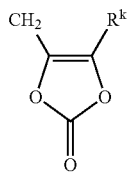

wherein $R^k$ is hydrogen, $C_{1-6}$alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such form, including pure isomeric forms. The different isomeric forms may be separated or resolved one from the other by conventional methods, or any given isomer may be obtained by conventional synthetic methods or by stereospecific or asymmetric syntheses.

One of skill in the readily appreciates that optimization for a given reaction may require some routine variation in reaction parameters such as reaction time, temperature, energy source, pressure, light, pressure, solvent or solvents used, co-reagents, catalysts, and the like.

Protective groups wherever found herein maybe designated by their specific formula or alternatively, maybe referred to generically by P or $P_n$ (wherein n is an integer). It is to be appreciated that where generic descriptors are used, that such descriptors are at each occurrence independent from each other. Thus, a compound with more than one of the same generic descriptors (e.g. P) does not indicate that each P is the same protective group, they maybe the same or different, so long as the group is suitable to the chemistry being employed. Where protection or deprotection is generically referred to, one of ordinary skill in the art will understand this to mean that suitable conditions are employed that will allow for the removal of the protecting group to be removed while minimizing reaction at other positions of the molecule, unless otherwise indicated. Many protective groups and protective group strategies are known to those of skill in the art in maybe found in numerous references including, Greene, et al. "Protective Groups in Organic Synthesis" (Published by Wiley-Interscience), which is herein incorporated by reference in its entirety.

Leaving groups wherever found herein maybe designated by a specific chemical formula, or alternatively, maybe generically referred to as L or Ln (wherein n is an integer). It is to be appreciated that where a generic descriptor is used, that such descriptors are at each occurrence independent from each other. Leaving groups can be single atoms such as Cl, Br, or I, or maybe a group such as $OSO_2CH_3$, $OC(=O)CH_3$, $O(C=O)CF_3$, $OSO_2CF_3$, and the like. Leaving groups may be formed during the course of a reaction and thus a compound containing a leaving group may not always be an isolated material but rather as a reactive intermediate. By way of non-limiting example, a carboxylic acid maybe reacted with a coupling reagent such as DCC, CDI, EDCI, isobutyl chloroformate, etc, and the corresponding relative intermediate thus formed is further reacted with the nucleophilic coupling partner. In such cases, one of skill in the art appreciates that the activation step maybe performed before the introduction of the nucleophilic coupling partner, or in some cases, even in the presence of the nucleophilic coupling partner (depending upon the identity of the particular activating agent, carboxylic acid and nuclephilic coupling partner used). One skilled in the art readily ascertains that leaving groups generally refer to atoms or groups which can be eliminated, substituted or otherwise dissociate during the course of the reaction.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

The compounds of this invention may also be used in the manufacture of medicaments useful in treating bacterial infections in humans or other mammals.

All publications, including but not limited to patents and patent applications, cited in this specification are herein incorporated by reference (whether specifically stated to be so or not) as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form, for example, of product, composition, process, or use claims.

The following examples illustrate the preparation of certain compounds of formula (I) and the activity of certain compounds of formula (I) against various bacterial organisms. Although specific examples are described in the schemes, one of skill in the art appreciates that the methods are more generally applicable.

One of skill in the art readily appreciates that although the following schemes describe specific examples, they maybe more generally applied to produce additional embodiments of this invention. Furthermore, the examples set forth below are illustrative of the present invention and are not intended to limit, in any way, the scope of the present invention.

The compounds of the present invention were prepared by the methods illustrated in Scheme I. Central linker units were either commercially available or prepared according to literature reports unless otherwise noted in the experimental section.

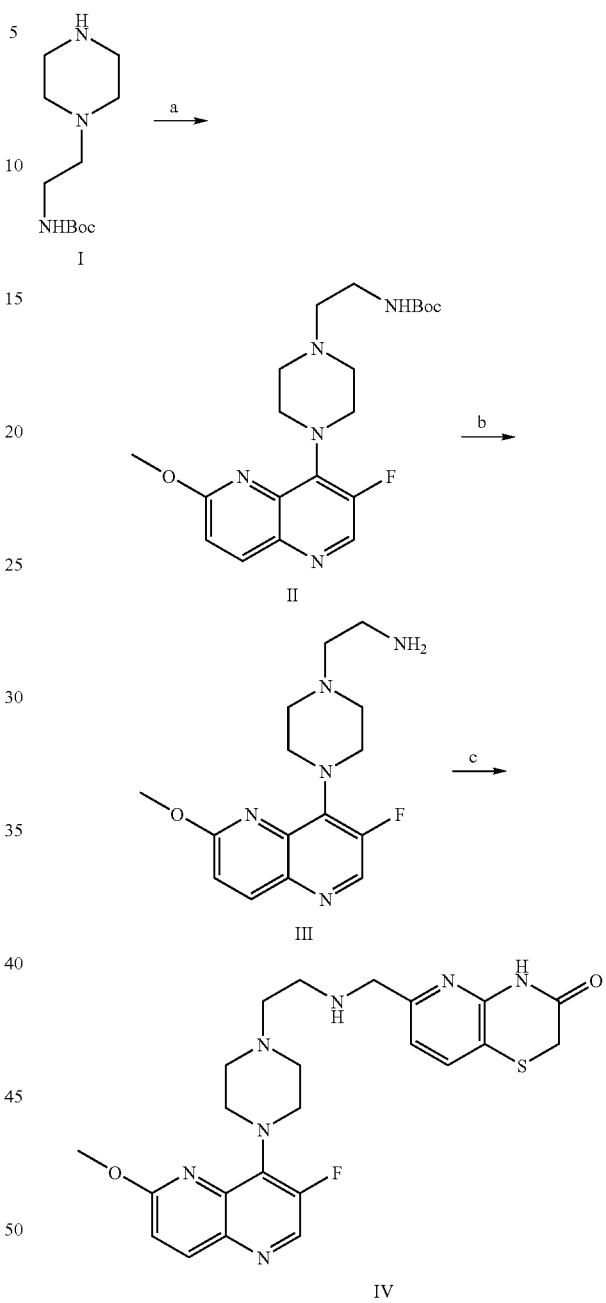

Scheme I

Reagents and conditions: (a) 8-bromo-7-fluoro-2-(methyloxy)-1,5-naphthyridine, rac-Binap, $Cs_2CO_3$, $Pd_2dba_3$, 18-C-6, dioxane, 100° C., sealed tube (b) 4M HCl in dioxane, MeOH, 25° C. (c) 3-oxo-3,4-dihydro-2H-pyrido[3,2-b][1,4]thiazine-6-carbaldehyde, $Na_2SO_4$, DCM/MeOH, 25° C. then $Na(OAc)_3BH$.

An appropriate amine containing central linker (I) was coupled to an aromatic bromide (II) or equivalent using standard Buchwald conditions. The Boc-protecting group was removed using conditions described by protecting group references like Kocienski or Greene, infra. The resulting free amine (III) underwent reductive amination with a suitable aromatic aldehyde generating final analog (IV).

General

Proton nuclear magnetic resonance ($^1$H NMR) spectra were recorded at 400 MHz, and chemical shifts are reported in parts per million (δ) downfield from the internal solvent standard CHCl$_3$ or MeOH. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuterochloroform and CD$_3$OD is tetradeuteromethanol. Mass spectra were obtained using electrospray (ES) ionization techniques. All temperatures are reported in degrees Celsius. E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

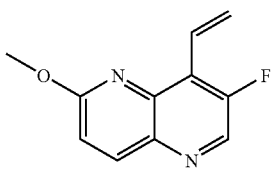

Preparation of
8-ethenyl-7-fluoro-2-(methyloxy)-1,5-naphthyridine (a) (2-[(6-Methoxypyridin-3-ylamino)methylene]malonic acid diethyl ester A solution of 5-amino-2-methoxypyridine (Aldrich, 100 g, 0.806 mole) and diethyl ethoxymethylenemalonate (Aldrich, 163 mL, 0.806 mole) in EtOH (1 L) was heated at reflux for 4 h, then was cooled to RT. Concentration to dryness gave the title compound (238 g, quantitative).

(b) 6-Methoxy-4-oxo-1,4-dihydro-[1,5]naphthyridine-3-carboxylic acid ethyl ester Dowtherm A (Fluka, 500 mL) was brought to boiling (250° C.) in a 2 L 3-neck flask fitted with a still-head and a reflux condenser. 2-[(6-Methoxypyridin-3-ylamino)methylene] malonic acid diethyl ester (100 g, 0.34 mole) was added portion-wise over 5 min. The solution was heated at reflux for an additional 15 min, allowing some solvent to distil over. The resulting solution was cooled to room temperature and diluted with hexane (750 mL). The mixture was cooled in ice for 1 h, then the brown solid was filtered off, washed with hexane, and dried under vacuum to afford the title compound (61.72 g, 73%).

(c) 4-Bromo-6-methoxy-[1,5]naphthyridine-3-carboxylic acid ethyl ester

A suspension of 6-methoxy-4-oxo-1,4-dihydro-[1,5]naphthyridine-3-carboxylic acid ethyl ester (74.57 g, 300 mmol) in dry DMF (260 mL) under argon was stirred efficiently* in a water bath (to maintain approximately room temperature—may need slight ice-cooling on a large scale). Phosphorus tribromide (30.0 mL, 316 mmol) was added dropwise over 15 min and stirring was continued for an additional 30 min. Water (1 L) was added, followed by saturated sodium carbonate solution to pH 7. The solid was collected by suction filtration, washed with water and dried under vacuum over phosphorus pentoxide to give the title compound (83.56 g, 90%).

(d) 4-Bromo-6-methoxy-[1,5]naphthyridine-3-carboxylic acid

2 N NaOH (300 mL, 600 mmol) was added dropwise over 30 min to a stirred solution of 4-bromo-6-methoxy-[1,5] naphthyridine-3-carboxylic acid ethyl ester (83.56 g, 268 mmol) in THF (835 mL). Stirring was continued overnight, at which time LC/MS showed that the saponification was complete. 2 N HCl was added to pH 6 and the THF was removed in vacuo. 2 N HCl was added to pH 2, then water (250 mL) was added, and the mixture was cooled thoroughly in ice. The solid was collected by suction filtration, washed with water and dried (first using a rotary evaporator at 50° C. and then under high vacuum at 50° C. overnight) to give the title compound (76.7 g, slightly over quantitative). This material was used without further purification.

(e) 4-Bromo-6-methoxy-[1,5]naphthyridin-3-ylamine

A suspension of 4-bromo-6-methoxy-[1,5]naphthyridine-3-carboxylic acid (50 g, 177 mmol) in dry DMF (600 mL) was treated with triethylamine (222.5 mL, 1.60 mole), tert-butanol (265 mL, 2.77 mole) and diphenylphosphoryl azide (41.75 mL, 194 mmol). The reaction was stirred under argon at 100° C. for 1 h, then was cooled to room temperature and concentrated to low volume. Ethyl acetate and excess aqueous sodium bicarbonate solution were added, the mixture was shaken, and some insoluble solid was filtered off. The layers were separated and the organic phase was washed with water (2×) and dried (MgSO$_4$). Concentration to dryness gave a crude mixture of 4-bromo-6-methoxy-[1,5]naphthyridin-3-ylamine (minor product) and (4-bromo-6-methoxy-[1,5] naphthyridin-3-ylamine)carbamic acid tert-butyl ester (major product) along with impurities.

Without further purification, this mixture was dissolved in CH$_2$Cl$_2$ (150 mL) and treated with trifluoroacetic acid (100 mL). The reaction was stirred for 3 h then was concentrated to dryness. The residue was partitioned between CHCl$_3$ and saturated sodium bicarbonate solution and the layers were separated. The aqueous phase was extracted with CHCl$_3$, and the combined organic fractions were dried (MgSO$_4$) and concentrated to low volume. The solid was collected by suction filtration, washed with a small volume of CHCl$_3$ and dried under vacuum to afford a first crop of the title compound (31.14 g). The filtrate was purified by flash chromatography on silica gel (30% EtOAc in CHCl$_3$) to afford further material (2.93 g, total=34.07 g, 76%). Alternatively, the filtrate was left at room temperature overnight and then filtered to give a second crop of the title compound (2.5 g).

(f) 4-Bromo-6-methoxy-[1,5]naphthyridine-3-diazonium tetrafluoroborate

A solution of 4-bromo-6-methoxy-[1,5]naphthyridin-3-ylamine (25.2 g, 99.2 mmol) in dry THF (400 mL) was maintained at −5° C. while nitrosonium tetrafluoroborate (12.9 g, 110 mmol) was added portion-wise over 30 min (approximately 2 g portions). The reaction was continued for an additional 1 h at −5° C., at which time TLC* and LC/MS indicated that the reaction was complete. The orange solid was collected by suction filtration, washed with ice-cold THF and dried under vacuum to provide the title compound (31.42 g, 90%).

(g) 4-Bromo-3-fluoro-6-methoxy-[1,5]naphthyridine

A suspension of 4-bromo-6-methoxy-[1,5]naphthyridine-3-diazonium tetrafluoroborate (31.42 g, 89.0 mmol) in decalin (mixed isomers, 500 mL) in a 2 L flask* was heated to 180° C. and held at this temperature for 5 min. The mixture was cooled and diluted with $CHCl_3$ (500 mL, to keep the product in solution), and the resulting mixture was stirred vigorously for 30 min to break up a black solid by-product. The mixture was then poured onto a column of silica gel and the column was eluted with $CHCl_3$ to remove decalin and then with 3% EtOAc/$CHCl_3$ to afford the title compound (9.16 g, 40%).

(h) 8-ethenyl-7-fluoro-2-(methyloxy)-1,5-naphthyridine

To a solution of 8-bromo-7-fluoro-2-(methyloxy)-1,5-naphthyridine (2.0 g, 7.81 mmol), potassium carbonate (1.08 g, 7.81 mmol), tetrakis-triphenylphosphine (90 mg, 0.08 mmol) in DME (60 mL) and $H_2O$ (20 mL) was added 2,4,6-trivinylcycloborane-pyridine complex (0.94 g, 3.91 mmol). After stirring for 10 h at 85° C. the reaction contents were concentrated and the product purified by chromatography (silica, 25% EtOAc in hexane) to give a low melting solid (1.43 g, 90%).

Preparation 2

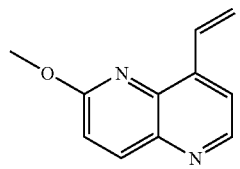

Preparation of 8-ethenyl-2-(methyloxy)-1,5-naphthyridine

To a solution of 6-(methyloxy)-1,5-naphthyridin-4-yl trifluoromethanesulfonate (from Prep. 2b) (5.0 g, 16.23 mmol) in DME (80 mL) and $H_2O$ (40 mL) was added trivinyl boronate (1.96 g, 8.1 mmol), $K_2CO_3$ (2.23 g, 16.23 mmol) and Pd(PPh$_3$)$_4$ (0.19 g, 0.16 mmol). After 3 h at 90° C. under $N_2$, the reaction solution was concentrated under vacuum and purified on silica (hexane/EtOAc, 4:1) to give the title compound as a yellow oil (2.44 g, 81%): LC/MS (m/z) (ES) 187 (M+H)$^+$.

Preparation of 3-Oxo-3,4-dihydro-2H-pyrido[3,2-b][1,4]thiazine-6-carboxaldehyde (a) Methyl 3-oxo-3,4-dihydro-2H-pyrido[3,2-b][1,4]thiazine-6-carboxylate A solution of ethyl 2-mercaptoacetate (1.473 mL) in DMF (48 mL) was ice-cooled and treated with sodium hydride (540 mg of a 60% dispersion in oil). After 1 h methyl 6-amino-5-bromopyridine-2-carboxylate (3 g) (T. R. Kelly and F. Lang, *J. Org. Chem.* 61, 1996, 4623-4633) was added and the mixture stirred for 16 h at room temperature. The solution was diluted with EtOAc (1 L), washed with water (3×300 mL), dried and evaporated to about 10 mL. The white solid was filtered off and washed with a little EtOAc to give the ester (0.95 g); LC/MS (APCI$^-$) m/z 223 ([M−H]$^-$, 100%).

(b) 3-Oxo-3,4-dihydro-2H-pyrido[3,2-b][1,4]thiazine-6-carboxylic acid

A solution of Methyl 3-oxo-3,4-dihydro-2H-pyrido[3,2-b][1,4]thiazine-6-carboxylate (788 mg) in dioxan (120 ml)/water (30 mL) was treated dropwise over 2 h with 0.5M NaOH solution (8 mL) and stirred overnight. After evaporation to approx. 3 ml, water (5 mL) was added and 2M HCl to pH4. The precipitated solid was filtered off, washed with a small volume of water and dried under vacuum to give a solid (636 mg); LC/MS (APCI$^-$) m/z 209 ([M−H]$^-$, 5%), 165([M−COOH]$^-$, 100%).

(c) 6-Hydroxymethyl-3-oxo-3,4-dihydro-2H-pyrido[3,2-b][1,4]thiazine

A solution of 3-oxo-3,4-dihydro-2H-pyrido[3,2-b][1,4]thiazine-6-carboxylic acid (500 mg) in THF (24 mL) with triethylamine (0.396 mL) was cooled to −10° C. and isobutyl chloroformate (0.339 ml) was added. After 20 minutes the suspension was filtered through kieselguhr into an ice-cooled solution of sodium borohydride (272 mg) in water (8 mL), the mixture stirred 30 minutes and the pH reduced to 7 with dilute HCl. The solvent was evaporated and the residue triturated under water. The product was filtered and dried under vacuum to give a white solid (346 mg); LC/MS (APCI$^-$) m/z 195 ([M−H]$^-$, 50%), 165(100%).

(d) 3-Oxo-3,4-dihydro-2H-pyrido[3,2-b][1,4]thiazine-6-carboxaldehyde

A solution of 6-hydroxymethyl-3-oxo-3,4-dihydro-2H-pyrido[3,2-b][1,4]thiazine (330 mg) in dichloromethane (30 mL)/THF (30 mL) was treated with manganese dioxide (730 mg) and stirred at room temperature. Further manganese dioxide was added after 1 h (730 mg) and 16 h (300 mg). After a total of 20 h the mixture was filtered through kieselguhr and the filtrate evaporated. The product was triturated with EtOAc/hexane (1:1) and collected to give a solid (180 mg); LC/MS (APCI$^-$) m/z 195 ([M−H]$^-$, 95%), 165 (100%).

Preparation 3

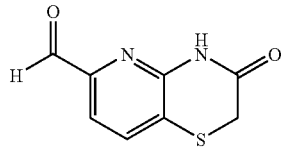

Preparation 4

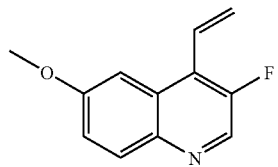

Preparation of 4-ethenyl-3-fluoro-6-(methyloxy)quinoline a) 4-Hydroxy-6-methoxy-quinoline-3-carboxylic acid ethyl ester A solution of 4-methoxyaniline (40 g, 0.32 mole) and diethyl ethoxymethylenemalonate (65 mL, 0.32 mole) in Dowtherm A (500 mL) was heated at reflux in a flask fitted with side-arm and condenser, and heating was continued until all the ethanol had distilled off (ca. 0.5 hr). The solution was cooled and pentane was added to give a sticky precipitate. The solvents were decanted off and the residue was treated with more pentane and allowed to stand overnight. The solid was filtered off and washed well with pentane to give the title compound (62.4 g; 78%, contains traces of Dowtherm A).

b) 4-Bromo-6-methoxy-quinoline-3-carboxylic acid ethyl ester $PBr_3$ (64.5 g, 22.5 mL, 0.239 mole) was added dropwise to a stirred, ice cold suspension of 4-hydroxy-6-methoxy-quinoline-3-carboxylic acid ethyl ester (59 g, 0.239 mole) in DMF (750 mL); the temperature rose to 15-20° C. for 30 min and then dropped to ca. 5° C. (the starting material dissolved fairly quickly and a new solid precipitated out). After 3 hr the solid was collected, washed sequentially with cold DMF, hexane, and water, then was dried at 40° C. in vacuo overnight to give the title compound (41 g, 78%): LC/MS (ES) m/e 310/312 (M+H)+.

c) 4-Bromo-6-methoxyquinoline-3-carboxylic acid

4-Bromo-6-methoxy-quinoline-3-carboxylic acid ethyl ester (41 g, 0.132 mole), partially dissolved in THF (600 mL), was treated dropwise with aqueous 2 M sodium hydroxide (198.4 mL, 0.396 mole). After 24 hr, the reaction was complete by TLC (2% MeOH/$CH_2Cl_2$). The mixture was neutralized with 5 M HCl then the THF was removed in vacuo. The residue was dissolved in water and acidified with 5 M HCl. The solid product was collected under suction, washed well with water, and dried in vacuo to give the title compound (34 g, 91%) as a white solid: MS (ES) m/e 282/284 (M+H)+.

d) (4-Bromo-6-methoxy-quinolin-3-yl)-carbamic acid tert-butyl ester

To a solution of 4-Bromo-6-methoxyquinoline-3-carboxylic acid (34 g, 0.121 mole), triethylamine (141 mL) and tert-butanol (181 mL) in dry DMF (400 mL) was added diphenylphosphoryl azide (36.6 g, 28.6 mL, 0.133 mole). The mixture was heated at 100° C. for 1 h (see Note), then cooled and concentrated. The residue was dissolved in $CH_2Cl_2$ and washed with water (some insoluble material was removed by filtration). The aqueous phase was extracted with dichloromethane and the combined organics were dried ($Na_2SO_4$) and concentrated. Chromatography on silica gel (1 kg, 1:1 ether/light petroleum ether) gave the carbamate (22.7 g, 53%): MS (ES) m/e 309/311 (M+H)+, 354/6.

Further elution with ether gave several mixed fractions then pure 3-amino-4-bromo-6-methoxyquinoline (2.0 g, 6.5%): MS (ES) m/e 309/311 (M+H)+, 254/6.

e) 3-Amino-4-bromo-6-methoxyquinoline (4-Bromo-6-methoxy-quinolin-3-yl)-carbamic acid tert-butyl ester (22.7 g, 0.0643 mole) was dissolved in $CH_2Cl_2$ (200 mL) and treated with trifluoroacetic acid (100 mL). After 3.5 hr at RT, the mixture was concentrated and the residue was dissolved in water. The solution was made basic with aqueous sodium carbonate. The precipitate was filtered off, washed with water, and dried at 40° C. in vacuo overnight, to give the title compound (16.46 g, 101%) as a white solid: MS (ES) m/e 254/256 (M+H)+.

f) 4-Bromo-3-methoxyquinolin-3-yl-diazonium tetrafluoroborate

3-Amino-4-bromo-6-methoxyquinoline (18.4 g, 0.0727 mole) was dissolved in dry THF (250 mL) and the solution was cooled to −8° C. (EtOH-ice bath). Nitrosonium tetrafluoroborate (9.34 g, 0.08 mole) was added in portions over 10 min, keeping the temperature less than −2° C. The mixture was stirred at −5 to 0° C. for 30 min, then the yellow precipitate was filtered off and washed sequentially with cold THF and hexane. Drying in vacuo gave the title compound (19.4 g, 76%) an insoluble orange-yellow solid.

g) 4-Bromo-3-fluoro-6-methoxyquinoline

A well stirred solution of decahydronaphthalene (mixed isomers, 120 mL) was heated to ca. 167-170° C. (internal temperature) and the diazonium tetrafluoroborate salt (6.0 g) was added portion-wise over 30 sec, when the solid turned black. The reaction mixture was immediately cooled and the decahydronaphthalene was filtered off. The filtrate was saved for further processing. The residue was extracted with dichloromethane (3×). Some insoluble material remained. The solution was concentrated and the residue was chromatographed on silica gel ($CH_2Cl_2$ then $CHCl_3$) to give the title compound (1.1 g) as a white solid: MS (ES) m/e 256/258 (M+H)+, Rt=2.65 min. About 4% of a dibromo impurity was present: MS (ES) m/e 316/318/320 (M+H)+ $R_t$=2.94 min.

The decahydronaphthalene solution was treated with excess ethereal HCl and the solid hydrochloride salt was collected and washed with hexane. This was converted to the free base by reaction with aqueous sodium carbonate followed by extraction with $CH_2Cl_2$. This gave additional title compound (0.87 g; total yield=1.97 g, 45%).

h) 4-ethenyl-3-fluoro-6-(methyloxy)quinoline

4-Bromo-3,fluoro-6-(methoxy)quinoline (2.3 mmol) in DME (26 mL) under argon, was treated with tetrakis(triphenylphosphine)palladium(0) (0.13 g, 0.115 mmol) and the mixture stirred at room temperature for 20 minutes. Anhydrous potassium carbonate (0.32 g, 2.3 mmol), water (7 mL), and vinylborane:pyridine complex (see F. Kerins and D O'Shea J. Org. Chem. 2002, 67, 4968-4971) (0.22 g, 0.92 mmol) were added and the mixture was heated at 100° C. for 2 hr. It was cooled, diluted with water and extracted with ether, dried over magnesium sulfate and evaporated to dryness. After work-up the product was chromatographed on silica gel, eluting with 10% methanol in DCM to afford a white solid (0.44 g, 90%). MS (+ve ion electrospray) m/z 203 (MH+).

Preparation 5

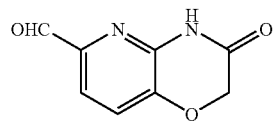

Preparation of 3-Oxo-3,4-dihydro-2H-pyrido[3,2-b][1,4]oxazine-6-carboxaldehyde a) 2-Bromo-5-hydroxy-6-nitropyridine 3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 mL). The solvent was removed in vacuo to afford material (30 g, 96%), which was used without further purification. MS (ES) m/z 219.0 (M+H)$^+$.

b) Ethyl (6-bromo-2-nitro-pyridin-3-yloxy)acetate

2-Bromo-5-hydroxy-6-nitropyridine (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et$_2$O. The precipitate was removed by suction filtration, and the filtrate was concentrated in vacuo to afford material (38 g, 89%), which was used without further purification; MS (ES) m/z 305.0 (M+H)$^+$.

c) 6-Bromo-4H-pyrido[3,2-b][1,4]oxazin-3-one

Ethyl (6-bromo-2-nitro-pyridin-3-yloxy)acetate (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%); MS (ES) m/z 229.0 (M+H)$^+$.

d) 6-((E)-Styryl)-4H-pyrido[3,2-b][1,4]oxazin-3-one

6-Bromo-4H-pyrido[3,2-b][1,4]oxazin-3-one (6.0 g, 26.3 mmole) and trans-2-phenylvinylboronic acid (3.9 g, 26.3 mmole) were dissolved in 1,4-dioxane (150 mL) and the solution was degassed with argon. (Ph$_3$P)$_4$Pd (230 mg, 0.2 mmole) was added, followed by a solution of potassium carbonate (6.9 g, 50 mmole) in H$_2$O (20 mL). The reaction was heated at reflux under argon overnight, then was cooled to room temperature and diluted with EtOAc (200 mL). The solution was washed sequentially with H$_2$O and brine, dried (Na$_2$SO$_4$), and concentrated in vacuo. The solid residue was purified by flash chromatography on silica gel (5-10% EtOAc/CHCl$_3$) to afford a solid (2.5 g, 38%). MS (ES) m/z 253.0 (M+H)$^+$.

e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (1.2 g, 4.8 mmole) was dissolved in CH$_2$Cl$_2$ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with Et$_2$O (50 mL). The collected solid was washed with additional Et$_2$O and dried to afford a solid (700 mg, 82%).

MS (ES) m/z 179.0 (M+H)$^+$.

Preparation 6

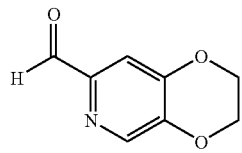

Preparation of 2,3-dihydro[1,4]dioxino[2,3-c]pyridine-7-carbaldehyde a) 5-Benzyloxy-2-hydroxymethyl-1H-pyridin-4-one A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 mL), and ethanol (20 mL) was heated to reflux overnight. The mixture was allowed to cool to room temperature then filtered. The resultant solid was washed with ether and dried in vacuo (5.9 g); MS (APCI+) m/z 232 (MH+).

b) (2,3-Dihydro-[1,4]dioxino[2,3-c]pyridin-7-yl)-methanol

A solution of 5-Benzyloxy-2-hydroxymethyl-1H-pyridin-4-one (2 g, 8.7 mmol) in water (220 mL) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 mL) then treated with potassium carbonate (2.9 g) and 1,2-dibromoethane (0.6 mL, 7 mmol). The mixture was heated at 85° C. overnight. The cooled mixture was evaporated onto silica and chromatographed eluting with 10-30% methanol in ethyl acetate affording a white solid (250 mg, 21%); MS (APCI+) m/z 168 (MH+).

c) 2,3-Dihydro-[1,4]dioxino[2,3-c]pyridine-7-carboxaldehyde

A solution of (2,3-Dihydro-[1,4]dioxino[2,3-c]pyridin-7-yl)-methanol (250 mg, 1.5 mmol) in dichloromethane (5 mL) was treated with manganese dioxide (650 mg, 7.5 mmol). After 3 days the mixture was filtered and evaporated affording a white solid (150 mg, 61%); MS (APCI+) m/z 166 (MH+).

EXAMPLE 1

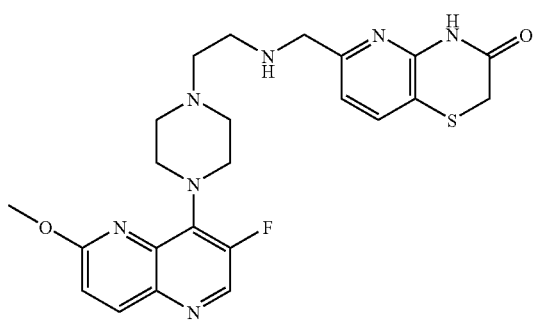

Preparation of 6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one (a) 1,1-dimethylethyl (2-{4-[3-fluoro-6-(methyloxy)-1,5-naphthyridin-4-yl]-1-piperazinyl}ethyl)carbamate

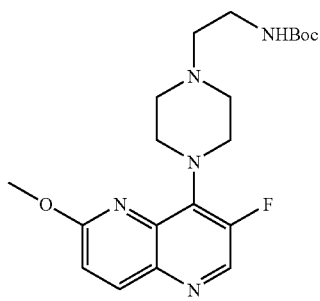

In a sealed tube, 8-bromo-7-fluoro-2-(methyloxy)-1,5-naphthyridine (1.1 g, 4.3 mmol), 1,1-dimethylethyl [2-(1-piperazinyl)ethyl]carbamate (1 g, 4.3 mmol), $Pd_2dba_3$ (271 mg, 0.262 mmol), rac-Binap (163 mg, 0.262 mmol), $Cs_2CO_3$ (2.98 mg, 9.2 mmol) and 18-C-6 (115 mg, 0.436 mmol) in dioxane (22 mL) were combined and flushed with $N_2$. After 15 min, the tube was sealed and heated to 100° C. while stirring rapidly. After 12 h, the solution was filtered, concentrated and the residue purified via column chromatography (silica, 1% MeOH in DCM (1% $NH_4OH$)) yielding the title compound (725 mg, 41%) as an orange oil: LCMS (ES) m/e 406 (M+H)$^+$.

(b) (2-{4-[3-fluoro-6-(methyloxy)-1,5-naphthyridin-4-yl]-1-piperazinyl}ethyl)amine

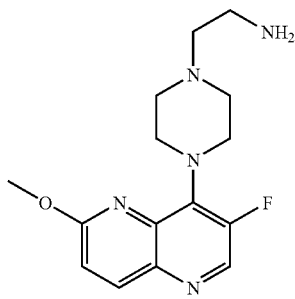

To a solution of 1,1-dimethylethyl (2-{4-[3-fluoro-6-(methyloxy)-1,5-naphthyridin-4-yl]-1-piperazinyl}ethyl)carbamate (725 mg, 1.79 mmol) in MeOH (9 mL) at 25° C. was added dropwise a 4M solution of HCl in dioxane (3.1 mL, 12.53 mmol). After 12 h, the solution was concentrated the residue neutralized using excess MP carbonate resin in DCM affording the free amine which was used without further purification: LCMS (ES) m/e 306 (M+H)$^+$.

(c) 6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one

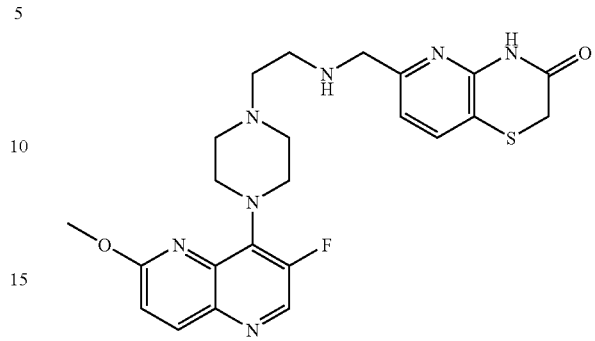

To a solution of (2-{4-[3-fluoro-6-(methyloxy)-1,5-naphthyridin-4-yl]-1-piperazinyl}ethyl)amine (155 mg, 0.508 mmol) in DCM-EtOH (5 mL, 1:1) were added $Na_2SO_4$ (144 mg, 1.02 mmol) and 3-oxo-3,4-dihydro-2H-pyrido[3,2-b][1,4]thiazine-6-carbaldehyde (99 mg, 0.508 mmol). After 12 h at 25° C., the imine was quenched by addition of $NaBH_4$ (29 mg, 0.762 mmol) in one portion. After an additional 1 h, the solution was partitioned between $H_2O$-DCM. The aqueous phase was washed several times with DCM and the combined organic fractions were dried ($Na_2SO_4$), concentrated and purified by column chromatography (silica, 1% MeOH in DCM (1% $NH_4OH$)) affording the title compound (73 mg, 30%) as a light yellow solid: LCMS (ES) m/e 484 (M+H)$^+$; $^1$H NMR ($CD_3OD$, 400 MHz) δ 8.46 (d, J=4.8 Hz, 1H), 8.11 (d, J=9.1 Hz, 1H), 7.74 (d, J=7.9 Hz, 1H), 7.13 (d, J=9.1 Hz, 1H), 7.07 (d, J=7.9 Hz, 1H), 4.06 (s, 3H), 3.92 (s, 2H), 3.83 (bs, 4H), 3.54 (bs, 2H), 2.88 (s, 2H), 2.66-2.72 (m, 6H).

EXAMPLE 2

Preparation of 6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one

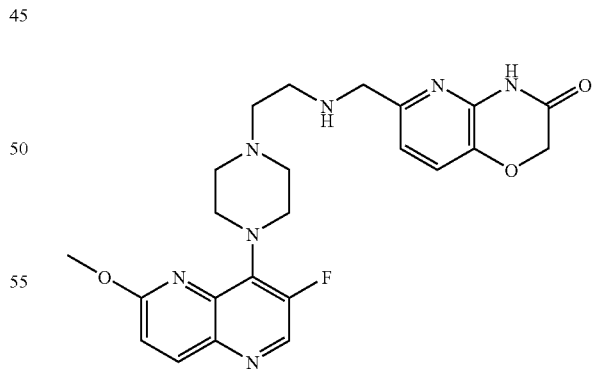

The title compound (99 mg, 42%) was prepared as a yellow solid according to Example 1, except substituting 3-oxo-3,4-dihydro-2H-pyrido[3,2-b][1,4]oxazine-6-carbaldehyde (91 mg, 0.508 mmol) for 3-oxo-3,4-dihydro-2H-pyrido[3,2-b][1,4]thiazine-6-carbaldehyde: LCMS (ES) m/e 468 (M+H)$^+$; $^1$H NMR ($CD_3OD$, 400 MHz) δ 8.45 (d, J=4.8 Hz, 1H), 8.11 (d, J=9.1 Hz, 1H), 7.30 (d, J=8.0 Hz, 1H), 7.13 (d, J=9.1 Hz, 1H), 7.01 (d, J=8.1 Hz, 1H), 4.66 (s, 2H), 4.06 (s, 3H), 3.83 (s, 6H), 2.82-2.85 (m, 2H), 2.64-2.71 (m, 6H).

EXAMPLE 3

Preparation of 6-{[(2-{4-[3-fluoro-6-(methyloxy)-4-quinolinyl]-1-piperazinyl}ethyl)amino]methyl}-2H-pyrido[3,2-b][1,4]thiazin-3(4H)-one

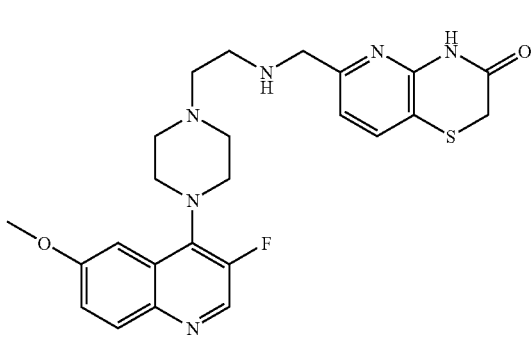

The title compound (59 mg, 28%) was prepared as a yellow solid according to Example 1, except substituting 4-bromo-3-fluoro-6-(methyloxy)quinoline (1.1 g, 4.36 mmol) for 8-bromo-7-fluoro-2-(methyloxy)-1,5-naphthyridine: LCMS (ES) m/e 483 (M+H)$^+$; $^1$H NMR (CD$_3$OD, 400 MHz) δ 8.50 (d, J=J=4.5 Hz, 1H), 7.89 (d, J=9.1 Hz, 1H), 7.71 (d, J=7.7 Hz, 1H), 7.43 (d, J=2.8, 1H), 7.36 (dd, J=2.9, 6.4 Hz, 1H), 7.06 (d, J=7.8 Hz, 1H), 3.97 (s, 3H), 3.86 (s, 2H), 3.53 (s, 2H), 3.44 (bs, 4H), 2.82-2.85 (m, 2H), 2.67-2.75 (m, 6H).

EXAMPLE 4

Preparation of 6-{[(2-{4-[3-fluoro-6-(methyloxy)-4-quinolinyl]-1-piperazinyl}ethyl)amino]methyl}-2H-pyrido[3,2-b][1,4]oxazin-3(4H)-one

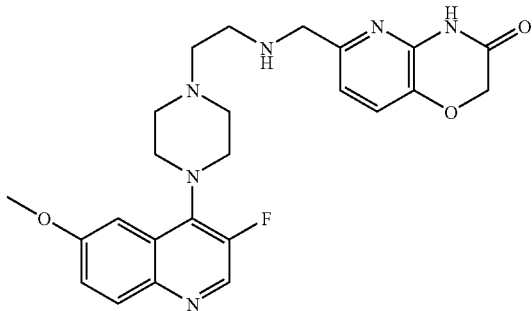

The title compound (76 mg, 36%) was prepared as a yellow solid according to Example 1, except substituting 4-bromo-3-fluoro-6-(methyloxy)quinoline (1.1 g, 4.36 mmol) for 8-bromo-7-fluoro-2-(methyloxy)-1,5-naphthyridine and 3-oxo-3,4-dihydro-2H-pyrido[3,2-b][1,4]oxazine-6-carbaldehyde (81 mg, 0.457 mmol) for 3-oxo-3,4-dihydro-2H-pyrido[3,2-b][1,4]thiazine-6-carbaldehyde: LCMS (ES) m/e 467 (M+H)$^+$; $^1$H NMR (CD$_3$OD, 400 MHz) δ 8.50 (d, J=4.5 Hz, 1H), 7.89 (d, J=9.2 Hz, 1H), 7.43 (d, J=2.8 Hz, 1H), 7.36 (dd, J=2.8, 6.4 Hz, 1H), 7.29 (d, J=8.0 Hz, 1H), 7.01 (d, J=8.0 Hz, 1H), 4.66 (s, 2H), 3.97 (s, 3H), 3.83 (s, 2H), 3.44 (bs, 4H), 2.82-2.85 (m, 2H), 2.67-2.74 (m, 6H).

EXAMPLE 5

Preparation of 6-{[(2-{4-[3-fluoro-6-(methyloxy)-1,5-naphthyridin-4-yl]-3-oxo-1-piperaziny}ethyl)amino]methyl}-2H-pyrido[3,2-b][1,4]thiazin-3(4H)-one

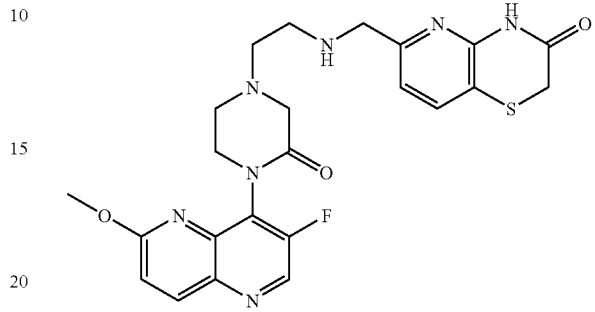

(a) 1,1-dimethylethyl [2-(3-oxo-1-piperazinyl)ethyl]carbamate

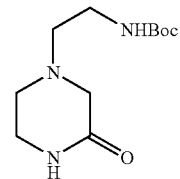

To a solution of (4-(2-aminium-ethyl)piperazin-one)(2-hydro-phthalazinate-1,4-dione) [3.4 g, 11.1 mmol, prepared according to Howell, R. C.; et. al. *Molecules* 2003, 8, 565.] in THF (60 mL) at 25° C. were added Et$_3$N (7.8 mL, 55.5 mmol) and Boc$_2$O (3 mL, 11.7 mmol). After 1 h, the solution was partitioned between H$_2$O-DCM. The aqueous phase was back-extracted several times with additional DCM and the combined organic fractions were dried (Na$_2$SO$_4$), concentrated and purified via column chromatography (silica, 1% MeOH in DCM (1% NH$_4$OH)) yielding the title compound (875 mg, 32%) as a clear oil: LCMS (ES) m/e 244 (M+H)$^+$.

(b) 6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]thiazin-3(4H)-one

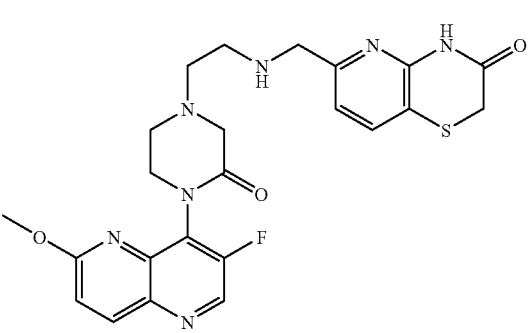

The title compound (81 mg, 33%) was prepared as a yellow solid according to Example 1, except substituting 1,1-dimethylethyl [2-(3-oxo-1-piperazinyl)ethyl]carbamate (875 mg, 3.62 mmol) for 1,1-dimethylethyl [2-(1-piperazinyl)ethyl]carbamate: LCMS (ES) m/e 498 (M+H)+; 1H NMR (CD3OD, 400 MHz) δ 8.83 (s, 1H), 8.29 (d, J=9.1 Hz, 1H), 7.72 (d, J=8.8 Hz, 1H), 7.24 (d, J=9.1 Hz, 1H), 7.06 (d, J=8.8 Hz, 1H), 4.09-4.20 (m, 1H), 4.06 (s, 3H), 3.88 (s, 2H), 3.70-3.79 (m, 1H), 3.51 (s, 2H), 3.45-3.49 (m, 1H), 3.39-3.41 (m, 1H), 3.01-3.07 (m, 2H), 2.84-2.88 (m, 2H), 2.78-2.80 (m, 2H).

EXAMPLE 6

Preparation of 6-{[(2-{4-[3-fluoro-6-(methyloxy)-1,5-naphtpyridin-4-yl]-3-oxo-1-piperazinyl}ethyl)amino]methyl}-2H-pyrido[3,2-b][1,4]oxazin-3(4H)-one

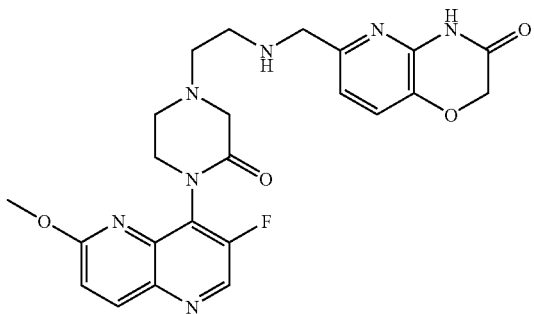

The title compound (22 mg, 9%) was prepared as a yellow solid according to Example 1, except substituting 1,1-dimethylethyl [2-(3-oxo-1-piperazinyl)ethyl]carbamate (875 mg, 3.62 mmol) for 1,1-dimethylethyl [2-(1-piperazinyl)ethyl]carbamate as well as 3-oxo-3,4-dihydro-2H-pyrido[3,2-b][1,4]oxazine-6-carbaldehyde (89 mg, 0.498 mmol) for 3-oxo-3,4-dihydro-2H-pyrido[3,2-b][1,4]thiazine-6-carbaldehyde: LCMS (ES) m/e 482 (M+H)+; 1H NMR (CD3OD, 400 MHz) δ 8.82 (s, 1H), 8.28 (d, J=9.1 Hz, 1H), 7.28 (d, J=8.0 Hz, 1H), 7.22 (d, J=9.1 Hz, 1H), 6.99 (d, J=8.0 Hz, 1H), 4.63 (s, 2H), 4.10-4.15 (m, 1H), 4.05 (s, 3H), 3.83 (s, 2H), 3.72-3.74 (m, 1H), 3.45 (AB quart., 2H), 3.00-3.06 (m, 2H), 2.76-2.84 (m, 4H).

EXAMPLE 7

Preparation of 4-{2-[(2,3-dihydro-[1,4]dioxino[2,3-c]pyridin-7-ylmethyl)amino]ethyl}-1-[3-fluoro-6-(methyloxy)-1,5-naphthyridin-4-yl]-2-piperazinone

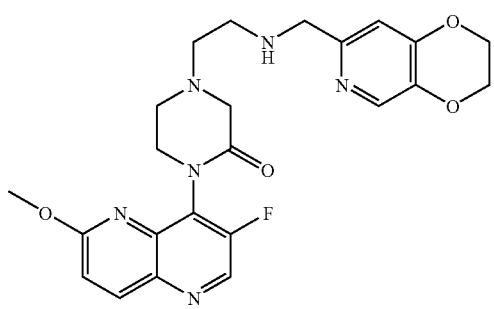

The title compound was prepared (25 mg, 11%) as a yellow solid according to Example 1, except substituting 1,1-dimethylethyl [2-(3-oxo-1-piperazinyl)ethyl]carbamate (875 mg, 3.62 mmol) for 1,1-dimethylethyl [2-(1-piperazinyl)ethyl]carbamate as well as 2,3-dihydro[1,4]dioxino[2,3-c]pyridine-7-carbaldehyde (81 mg, 0.492 mmol) for 3-oxo-3,4-dihydro-2H-pyrido[3,2-b][1,4]thiazine-6-carbaldehyde: LCMS (ES) m/e 469 (M+H)+; 1H NMR (CD3OD, 400 MHz) δ 8.85 (d, J=5.4 Hz, 1H), 8.29 (d, J=8.1 Hz, 1H), 8.00 (d, J=10.9 Hz, 1H), 7.23 (d, J=8.1 Hz, 1H), 6.94 (d, J=4.7 Hz, 1H), 4.25-4.36 (m, 4H), 4.09 (s, 2H), 4.03-4.08 (m, 1H), 4.07 (s, 3H), 3.72-3.79 (m, 2H), 3.62-3.74 (m, 1H), 3.18-3.23 (m, 1H), 2.91-2.99 (m, 3H), 2.65-2.79 (m, 1H), 2.52-2.61 (m, 1H).

EXAMPLE 8

Preparation of 6-{[(2-{4-[6-(methyloxy)-1,5-naphthyridin-4-yl]-3-oxo-1-piperazinyl}ethyl)amino]methyl}-2H-pyrido[3,2-b][1,4]thiazin-3(4H)-one (a) 1,1-dimethylethyl (2-{4-[6-(methyloxy)-1,5-naphthyridin-4-yl]-3-oxo-1-piperazinyl}ethyl)carbamate

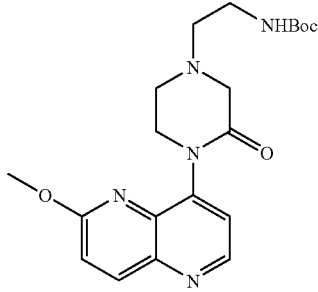

In a sealed tube 1,1-dimethylethyl [2-(3-oxo-1-piperazinyl)ethyl]carbamate (1.7 g, 7.02 mmol), 6-(methyloxy)-1,5-naphthyridin-4-yl trifluoromethanesulfonate (2.17 g, 7.02 mmol), Pd2dba3 (436 mg, 0.421 mmol), rac-Binap (262 mg, 0.421 mmol), Cs2CO3 (4.81 g, 14.75 mmol) and 18-C-6 (186 mg, 0.702 mmol) in dioxane (35 mL) were combined and flushed with N2. After 15 min, the tube was sealed and heated to 100° C. while stirring rapidly. After 12 h, the solution was filtered, concentrated and the residue purified via column chromatography (silica, 1% MeOH in DCM (1% NH4OH)) yielding the title compound (1.5 g, 53%) as a burgundy foam: LCMS (ES) m/e 402 (M+H)+.

(b) 4-(2-aminoethyl)-1-[6-(methyloxy)-1,5-naphthyridin-4-yl]-2-piperazinone

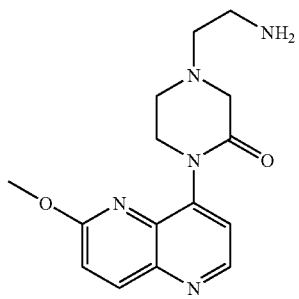

To a solution of 1,1-dimethylethyl (2-{4-[6-(methyloxy)-1,5-naphthyridin-4-yl]-3-oxo-1-piperazinyl}ethyl)carbamate (1.5 g, 3.74 mmol) in MeOH (19 mL) at 25° C. was added dropwise, a solution of HCl in dioxane (6.5 mL, 26.18 mmol, 4M HCl in dioxane). After 12 h, the solution was concentrated and the residue neutralized with excess MP carbonate resin affording the free amine (1.1 mg, 98%) as a red oil which was used without further purification: LCMS (ES) m/e 302 (M+H)+.

(c) 6-{[(2-{4-[6-(methyloxy)-1,5-naphthyridin-4-yl]-3-oxo-1-piperazinyl}ethyl)amino]methyl}-2H-pyrido[3,2-b][1,4]thiazin-3(4H)-one

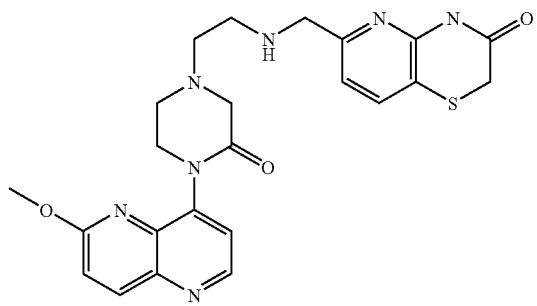

To a solution of 4-(2-aminoethyl)-1-[6-(methyloxy)-1,5-naphthyridin-4-yl]-2-piperazinone (168 mg, 0.558 mmol) in DCM-EtOH (6 mL, 5:1) at 25° C. were added Na$_2$SO$_4$ (158 mg, 1.11 mmol) and 3-oxo-3,4-dihydro-2H-pyrido[3,2-b][1,4]thiazine-6-carbaldehyde (108 mg, 0.558 mmol). After 12 h, Na(OAc)$_3$BH (177 mg, 0.837 mmol) was added and following an additional 2 h, the solution was partitioned between DCM-H$_2$O. The aqueous phase was extracted several times with DCM and the combined organic fractions were dried (Na$_2$SO$_4$), concentrated and purified via column chromatography (silica, 1% MeOH in DCM (1% NH$_4$OH)) affording the title compound (100 mg, 37%) as a yellow solid: LCMS (ES) m/e 480 (M+H)+; $^1$H NMR (CD$_3$OD, 400 MHz) δ 8.81 (d, J=4.7 Hz, 1H), 8.28 (d, J=9.1 Hz, 1H), 7.72 (d, J=7.8 Hz, 1H), 7.71 (d, J=4.7 Hz, 1H), 7.28 (d, J=9.1 Hz, 1H), 7.06 (d, J=8.1 Hz, 1H), 4.04 (s, 3H), 3.92-3.94 (m, 2H), 3.88 (s, 2H), 3.51 (s, 2H), 3.34 (2H), 3.00-3.03 (m, 2H), 2.82-2.84 (m, 2H), 2.77-2.79 (m, 2H).

EXAMPLE 9

Preparation of 6-{[(2-{4-[6-(methyloxy)-1,5-naphthyridin-4-yl]-3-oxo-1-piperazinyl}ethyl)amino]methyl}-2H-pyrido[3,2-b][1,4]oxazin-3(4H)-one

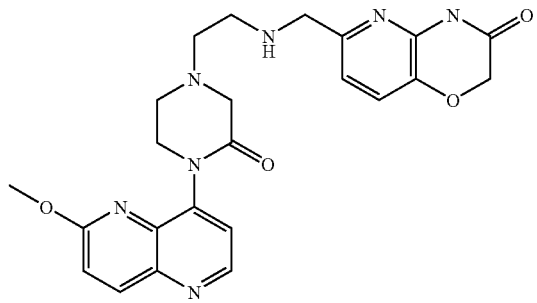

The title compound (20 mg, 7%) was prepared as an orange solid according to Example 8, except substituting 3-oxo-3,4-dihydro-2H-pyrido[3,2-b][1,4]oxazine-6-carbaldehyde (118 mg, 0.664 mmol) for 3-oxo-3,4-dihydro-2H-pyrido[3,2-b][1,4]thiazine-6-carbaldehyde: LCMS (ES) m/e 464 (M+H)+; $^1$H NMR (CD$_3$OD, 400 MHz) δ 8.80 (d, J=4.7 Hz, 1H), 8.27 (d, J=9.1 Hz, 1H), 7.68 (d, J=4.7 Hz, 1H), 7.28 (d, J=8.1 Hz, 1H), 7.25 (d, J=9.2 Hz, 1H), 6.99 (d, J=8.0 Hz, 1H), 4.62 (s, 2H), 4.02 (s, 3H), 3.89-3.92 (m, 2H), 3.81 (s, 2H), 3.37 (s, 2H), 2.99-3.01 (m, 2H), 2.74-2.82 (m, 4H).

EXAMPLE 10

Preparation of 4-{2-[(2,3-dihydro[1,4]dioxino[2,3-c]pyridin-7-ylmethyl)amino]ethyl}-1-[6-(methyloxy)-1,5-naphthyridin-4-yl]-2-piperazinone

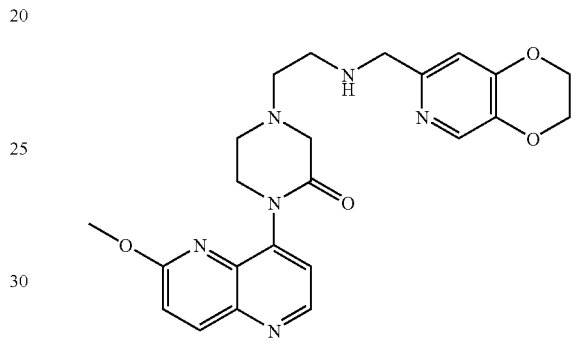

The title compound was prepared as a yellow solid according to Example 8, except substituting 2,3-dihydro[1,4]dioxino[2,3-c]pyridine-7-carbaldehyde (110 mg, 0.664 mmol) for 3-oxo-3,4-dihydro-2H-pyrido[3,2-b][1,4]thiazine-6-carbaldehyde: LCMS (ES) m/e 451 (M+H)+; $^1$H NMR (CD$_3$OD, 400 MHz) δ 8.81 (d, J=4.8 Hz, 1H), 8.27 (d, J=9.1 Hz, 1H), 8.03 (s, 1H), 7.67 (d, J=4.7 Hz, 1H), 7.26 (d, J=9.1 Hz, 1H), 6.99 (s, 1H), 4.36-4.38 (m, 2H), 4.29-4.32 (m, 2H), 4.04 (s, 3H), 3.90-3.93 (m, 2H), 3.80 (s, 2H), 3.40 (s, 2H), 2.98-3.01 (m, 2H), 2.75-2.80 (m, 4H).

EXAMPLE 11

Preparation of 6-{[(2-{4-[6-(methyloxy)-1,5-naphthyridin-4-yl]-2-oxo-1-piperazinyl}ethyl)amino]methyl}-2H-pyrido[3,2-b][1,4]thiazin-3(4H)-one

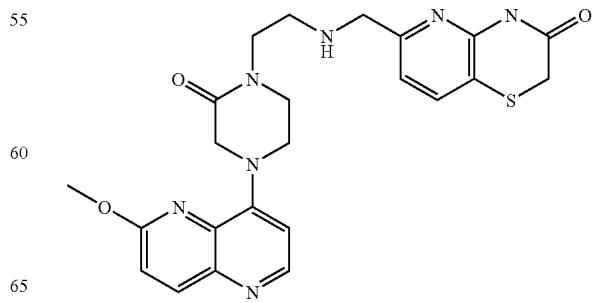

(a) 2-chloro-N,N-bis[2-(1,3-dioxo-1,3-dihydro-2H-isoindol-2-yl)ethyl]acetamide

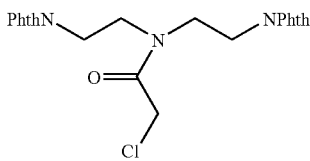

To a solution chloroacetyl chloride (1.2 mL, 15.2 mmol) in DCM (65 mL) at 0° C. was added dropwise a solution of 2,2'-(iminodi-2,1-ethanediyl)bis(1H-isoindole-1,3(2H-dione) (5 g, 13.7 mmol) [prepared according to Anelli, P. L.; et. al. *J. Org. Chem.* 1984 49, 4197.] and Et$_3$N (2.5 mL, 17.9 mmol) in DCM (65 mL). After 1 h, the solution was partitioned between H$_2$O-DCM and the aqueous phase was washed several times with DCM. The combined organic fractions were dried (Na$_2$SO$_4$), concentrated and purified via column chromatography (silica, 5% MeOH in DCM (NH$_4$OH)) yielding the title compound (5.9 g, 98%) as a yellow foam: LCMS (ES) m/e 440 (M+H)$^+$.

(b) 2-[2-(2-oxo-1-piperazinyl)ethyl]-1H-isoindole-1,3(2H)-dione

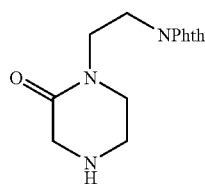

To a solution of 2-chloro-N,N-bis[2-(1,3-dioxo-1,3-dihydro-2H-isoindol-2-yl)ethyl]acetamide (2 g, 4.55 mmol) in EtOH (230 mL) was added hydrazine hydrate (213 μL, 6.83 mmol). After 12 h at 85° C., the solution was concentrated and the residue purified via column chromatography (silica, 3% MeOH in DCM (1% NH$_4$OH)) yielding the title compound (428 mg, 34%) as a yellow foam: LCMS (ES) m/e 274 (M+H)$^+$.

(c) 2-(2-{4-[6-(methyloxy)-1,5-naphthyridin-4-yl]-2-oxo-1-piperazinyl}ethyl)-1H-isoindole-1,3(2H)-dione

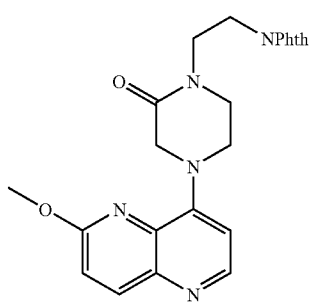

A solution of 6-(methyloxy)-1,5-naphthyridin-4-yl trifluoromethanesulfonate (169 mg, 0.55 mmol) and 2-[2-(2-oxo-1-piperazinyl)ethyl]-1H-isoindole-1,3(2H)-dione (150 mg, 0.55 mmol) in EtOH (2 mL) were stirred at 85° C. After 12 h, the solution was concentrated and the residue purified via column chromatography (silica, 0-8% MeOH in DCM (1% NH$_4$OH)) yielding the title compound (100 mg, 42%) as a light yellow solid: LCMS (ES) m/e 432 (M+H)$^+$.

(d) 1-(2-aminoethyl)-4-[6-(methyloxy)-1,5-naphthyridin-4-yl]-2-piperazinone

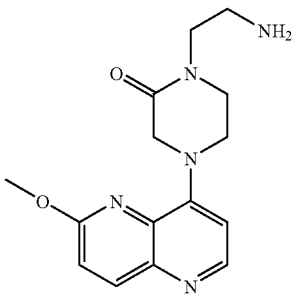

To a solution of 2-(2-{4-[6-(methyloxy)-1,5-naphthyridin-4-yl]-2-oxo-1-piperazinyl}ethyl)-1H-isoindole-1,3(2H)-dione (100 mg, 0.232 mmol) in EtOH (2 mL) was added hydrazine hydrate (120 μL, 3.85 mmol). After 2 h at 85° C., the solution was concentrated and the residue purified by column chromatography (silica, 5-10% MeOH in DCM (1% NH$_4$OH)) yielding the title compound (46 mg, 66%) as a yellow oil: LCMS (ES) m/e 302 (M+H)$^+$.

(e) 6-{[(2-{4-[6-(methyloxy)-1,5-naphthyridin-4-yl]-2-oxo-1-piperazinyl}ethyl)amino]methyl}-2H-pyrido[3,2-b][1,4]thiazin-3(4H)-one

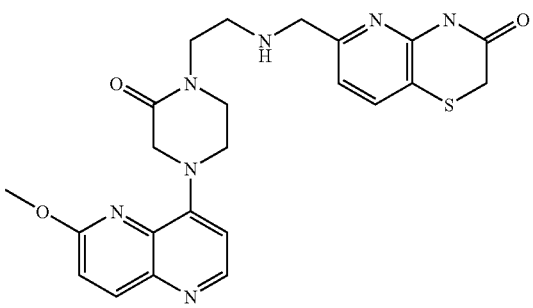

To a solution of 1-(2-aminoethyl)-4-[6-(methyloxy)-1,5-naphthyridin-4-yl]-2-piperazinone (46 mg, 0.15 mmol) in DCM-EtOH (2 mL, 1:1) were added NaHCO$_3$ (32 mg, 0.38 mmol) and 3-oxo-3,4-dihydro-2H-pyrido[3,2-b][1,4]thiazine-6-carbaldehyde (29 mg, 0.15 mmol). After 12 h, NaBH(OAc)$_3$ (38 mg, 0.15 mmol) was added. After an additional 2 h the solution was partitioned between NaHCO$_3$ (sat)-DCM. The aqueous phase was extracted several times with DCM and the combined organic fractions were dried (Na$_2$SO$_4$), concentrated and purified via column chromatography (silica, 0-7% MeOH in DCM (1% NH$_4$OH)) yielding the title compound (48 mg, 67%) as a yellow solid: LCMS (ES) m/e 480 (M+H)$^+$; $^1$H NMR (CD$_3$OD, 400 MHz) δ 8.44 (d, J=5.3 Hz, 1H), 8.12 (d, J=9.0 Hz, 1H), 7.63 (d, J=7.8 Hz, 1H), 7.17 (d, J=9.0 Hz, 1H), 7.00 (d, J=7.8 Hz, 1H), 6.96 (d, J=5.2 Hz, 1H), 4.21 (s, 2H), 4.19-4.22 (m, 2H), 4.03 (s, 3H), 3.82 (s, 2H), 3.69-3.74 (m, 4H), 3.67 (s, 2H), 2.90-2.93 (m, 2H).

EXAMPLE 12

Preparation of 1-{2-[(2,3-dihydro[1,4]dioxino[2,3-c]pyridin-7-ylmethyl)amino]ethyl}-4-[6-(methyloxy)-1,5-naphtpyridin-4-yl]-2-piperazinone

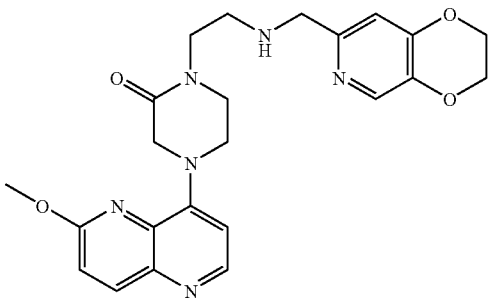

The title compound (19.4 mg, 59 mmol) was prepared as a yellow solid according to Example 11, except substituting 2,3-dihydro[1,4]dioxino[2,3-c]pyridine-7-carbaldehyde (12 mg, 0.073 mmol) for 3-oxo-3,4-dihydro-2H-pyrido[3,2-b][1,4]thiazine-6-carbaldehyde: LCMS (ES) m/e 451 (M+H)$^+$; $^1$H NMR (CD$_3$OD, 400 MHz) δ 8.44 (bs, 1H), 8.12 (d, J=8.9 Hz, 1H), 7.95 (s, 1H), 7.17 (d, J=9.0 Hz, 1H), 6.95 (bs, 2H), 4.21-4.36 (m, 8H), 4.03 (s, 3H), 3.77 (s, 2H), 3.73 (s, 2H), 3.64-3.67 (m, 2H), 2.85-2.89 (m, 2H).

EXAMPLE 13

EXAMPLE 13

Preparation of 6-{[(2-{1-[3-fluoro-6-(methyloxy)-1,5-naphthyridin-4-yl]-4-piperidinyl}ethyl)amino]methyl}-2H-pyrido[3,2-b][1,4]thiazin-3(4H)-one

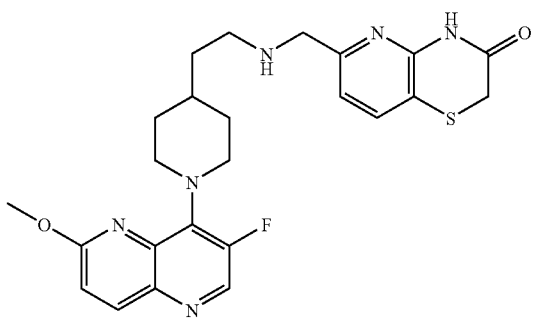

The title compound (62 mg, 22%) was prepared as a yellow foam according to Example 1, except substituting 1,1-dimethylethyl [2-(4-piperidinyl)ethyl]carbamate (1 g, 4.38 mmol) [prepared according to Ambler, J.; et. al. *Bioorg. Med. Chem. Lett.* 1999, 9, 9, 1317.] for 1,1-dimethylethyl [2-(1-piperazinyl)ethyl]carbamate: LCMS (ES) m/e 483 (M+H)$^+$; $^1$H NMR (400 MHz, CD$_3$OD) δ 8.42 (d, J=4.9 Hz, 1H), 8.08 (d, J=9.0 Hz, 1H), 7.71 (d, J=7.8 Hz, 1H), 7.11 (d, J=9.0 Hz, 1H), 7.04 (d, J=7.8 Hz, 1H), 4.10-4.13 (m, 2H), 4.06 (s, 3H), 3.82 (s, 2H), 3.53 (s, 2H), 3.34-3.37 (m, 2H), 2.71-2.75 (m, 2H), 1.82-1.85 (m, 2H), 1.51-1.63 (m, 5H).

EXAMPLE 14

Preparation of 6-{[(2-{1-[3-fluoro-6-(methyloxy)-1,5-naphthyridin-4-yl]-4-piperidinyl}ethyl)amino]methyl}-2H-pyrido[3,2-b][1,4]oxazin-3(4H)-one

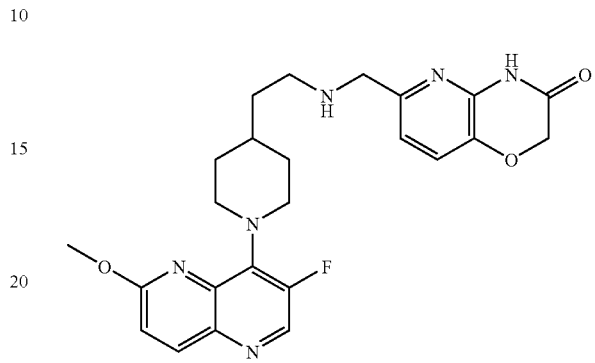

The title compound (28 mg, 10%) was prepared as a yellow foam according to Example 1, except substituting 1,1-dimethylethyl [2-(4-piperidinyl)ethyl]carbamate (1 g, 4.38 mmol) [prepared according to Ambler, J.; et. al. *Bioorg. Med. Chem. Lett.* 1999, 9, 9, 1317.] for 1,1-dimethylethyl [2-(1-piperazinyl)ethyl]carbamate as well as 3-oxo-3,4-dihydro-2H-pyrido[3,2-b][1,4]oxazine-6-carbaldehyde (105 mg, 0.590 mmol) for 3-oxo-3,4-dihydro-2H-pyrido[3,2-b][1,4]thiazine-6-carbaldehyde: LCMS (ES) m/e 467 (M+H)$^+$; $^1$H NMR (400 MHz, CDCl$_3$) δ 8.42 (d, J=4.9 Hz, 1H), 8.09 (d, J=9.0 Hz, 1H), 7.29 (d, J=8.0 Hz, 1H), 7.12 (d, J=9.0 Hz, 1H), 6.99 (d, J=8.0 Hz, 1H), 4.66 (s, 2H), 4.07-4.13 (m, 2H), 4.06 (s, 3H), 3.80 (s, 2H), 3.35-3.50 (m, 2H), 2.71-2.75 (m, 2H), 1.83-1.86 (m, 2H), 1.52-1.63 (m, 5H).

EXAMPLE 15

Preparation of 6-{[(2-{1-[3-fluoro-6-(methyloxy)-4-quinolinyl]-4-piperidinyl}ethyl)amino]methyl}-2H-pyrido[3,2-b][1,4]thiazin-3(4H)-one

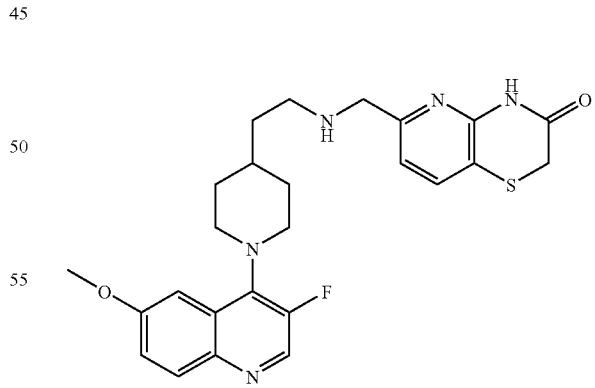

The title compound (100 mg, 32%) was prepared as a yellow solid according to Example 1, except substituting 1,1-dimethylethyl [2-(4-piperidinyl)ethyl]carbamate (2 g, 8.77 mmol) [prepared according to Ambler, J.; et. al. *Bioorg. Med. Chem. Lett.* 1999, 9, 9, 1317.] for 1,1-dimethylethyl [2-(1-piperazinyl)ethyl]carbamate as well as 4-bromo-3-fluoro-6-(methyloxy)quinoline (2.25 g, 8.77 mmol) for 8-bromo-7-fluoro-2-(methyloxy)-1,5-naphthyridine: LCMS (ES) m/e 466 (M+H)+; 1H NMR (400 MHz, CD3OD) δ 8.45 (d, J=4.6 Hz, 1H), 7.87 (d, J=9.1 Hz, 1H), 7.72 (d, J=7.6 Hz, 1H), 7.41 (d, J=2.7 Hz, 1H), 7.34 (dd, J=2.8, 6.3 Hz, 1H), 7.05 (d, J=7.8 Hz, 1H), 3.97 (s, 3H), 3.86 (s, 2H), 3.54 (s, 2H), 3.47-3.50 (m, 2H), 3.30-3.31 (m, 1H), 2.74-2.78 (m, 2H), 1.87-1.91 (m, 2H), 1.65-1.68 (m, 3H), 1.53-1.56 (m, 3H).

EXAMPLE 16

Preparation of 6-{[(2-{1-[3-fluoro-6-(methyloxy)-4-quinolinyl]-4-piperidinyl}ethyl)amino]methyl}-2H-pyrido[3,2-b][1,4]oxazin-3(4H)-one

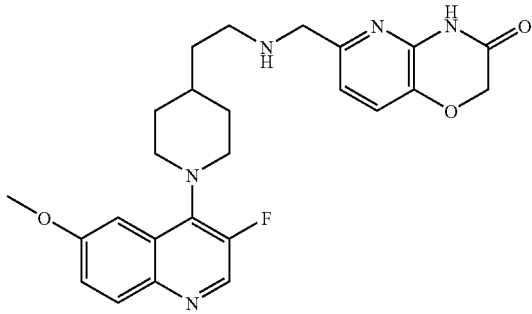

The title compound (100 mg, 33%) was prepared as a yellow solid according to Example 1, except substituting the following three reagents: 1,1-dimethylethyl [2-(4-piperidinyl)ethyl]carbamate (1 g, 4.38 mmol) [prepared according to Ambler, J.; et. al. *Bioorg. Med. Chem. Lett.* 1999, 9, 9, 1317.] for 1,1-dimethylethyl [2-(1-piperazinyl)ethyl]carbamate, 4-bromo-3-fluoro-6-(methyloxy)quinoline (2.25 g, 8.77 mmol) for 8-bromo-7-fluoro-2-(methyloxy)-1,5-naphthyridine and 3-oxo-3,4-dihydro-2H-pyrido[3,2-b][1,4]oxazine-6-carbaldehyde (117 mg, 0.657 mmol) for 3-oxo-3,4-dihydro-2H-pyrido[3,2-b][1,4]thiazine-6-carbaldehyde: LCMS (ES) m/e 482 (M+H)+; 1H NMR (400 MHz, CD3OD) δ 8.47 (d, J=4.5 Hz, 1H), 7.87 (d, J=9.1 Hz, 1H), 7.40 (d, J=2.7 Hz, 1H), 7.34 (dd, J=2.7, 6.3 Hz, 1H), 7.29 (d, J=8.0 Hz, 1H), 6.99 (d, J=8.0 Hz, 1H), 4.66 (s, 2H), 3.97 (s, 3H), 3.79 (s, 2H), 3.35-3.50 (m, 2H), 3.26-3.30 (m, 2H), 2.71-2.75 (m, 2H), 1.87-1.90 (m, 2H), 1.62-1.66 (m, 3H), 1.52-1.55 (m, 2H).

EXAMPLE 17

Preparation of 6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one (a) 2-[4-hydroxy-1-(phenylmethyl)-4-piperidinyl]acetamide

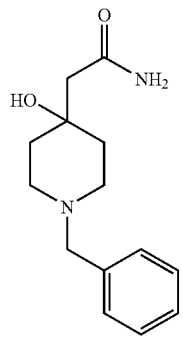

A solution of ethyl [4-hydroxy-1-(phenylmethyl)-4-piperidinyl]acetate (15 g, 54.15 mmol) [prepared according to Caroon, J. M.; et al. *J. Med. Chem.* 1981, 24,1320.] in 7N NH3-MeOH (16 mL) was heated to 100° C. in a sealed tube for 3d. The solution was cooled and concentrated and the residue washed with DCM providing the title compound (4 g, 30%) as a white solid which was used directly without further purification: LCMS (ES) m/e 249 (M+H)+.

(b) 4-(2-aminoethyl)-1-(phenylmethyl)-4-piperidinol

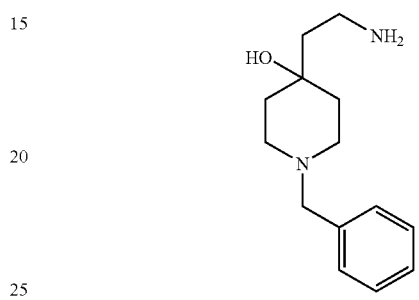

To a solution of LiAlH4 (1.8 g, 0.048 mmol) in THF (40 mL) at 0° C. was added dropwise via addition funnel a solution of 2-[4-hydroxy-1-(phenylmethyl)-4-piperidinyl]acetamide (4 g, 0.016 mmol) in THF (40 mL). The solution warmed to 25° C. and was then heated to reflux for 12 h. After cooling, the solution was then carefully quenched with a saturated solution of sodium potassium tartrate and extracted several times with DCM. The combined organic fractions were dried (Na2SO4) and the resulting residue was used directly without further purification: LCMS (ES) m/e 236 (M+H)+.

(c) 1,1-dimethylethyl {2-[4-hydroxy-1-(phenylmethyl)-4-piperidinyl]ethyl}carbamate

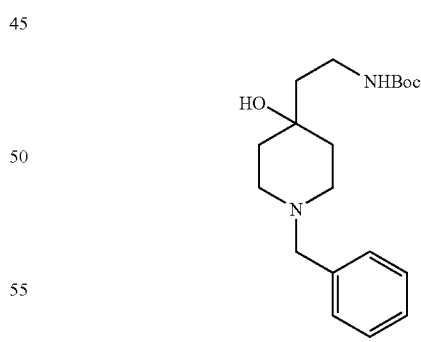

To a solution of 4-(2-aminoethyl)-1-(phenylmethyl)-4-piperidinol (2.7 g, 11.5 mmol) in THF/CH3CN (57 mL, 1:1) was added Boc2O dropwise. After 0.5 h, the solution was concentrated and the residue purified via column chromatography (silica, 2% MeOH in DCM (1% NH4OH)) yielding the title compound (3.2 g, 83%) as a yellow oil: LCMS (ES) m/e 336 (M+H)+.

33

(d) 1,1-dimethylethyl [2-(4-hydroxy-4-piperidinyl)ethyl]carbamate

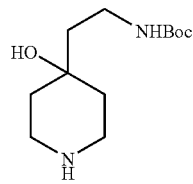

A solution of 1,1-dimethylethyl {2-[4-hydroxy-1-(phenylmethyl)-4-piperidinyl]ethyl}carbamate (3.2 g, 9.5 mmol) and Pd(OH)$_2$ (1.92 g, 60 wt %) in EtOH (50 mL) was hydrogenated using a Parr Shaker under 50 psi. After 12 h, the solution was filtered through Celite® and concentrated yielding the title compound (2.33 g, quant.) as a yellow oil: LCMS (ES) m/e 245 (M+H)$^+$.

(e) 6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one

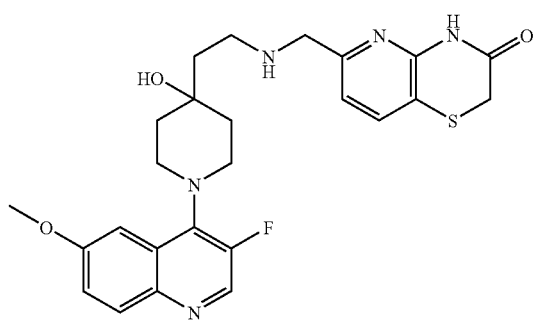

The title compound (60 mg, 21%) was prepared as a yellow solid according to Example 1, except substituting 1,1-dimethylethyl [2-(4-hydroxy-4-piperidinyl)ethyl]carbamate (1.5 g, 6.15 mmol) for 1,1-dimethylethyl [2-(1-piperazinyl)ethyl]carbamate as well as 4-bromo-3-fluoro-6-(methyloxy)quinoline (1.57 g, 6.15 mmol) for 8-bromo-7-fluoro-2-(methyloxy)-1,5-naphthyridine: LCMS (ES) m/e 498 (M+H)$^+$; $^1$H NMR (400 MHz, CD$_3$OD) δ 8.48 (d, J=4.7 Hz, 1H), 7.86 (d, J=9.1 Hz, 1H), 7.60 (d, J=7.8 Hz, 1H), 7.39 (d, J=2.6 Hz, 1H), 7.34 (dd, J=2.7, 6.4 Hz, 1H), 7.04 (d, J=7.8 Hz, 1H), 3.96 (s, 3H), 3.83 (s, 2H), 3.56-3.60 (m, 2H), 3.52 (s, 2H), 3.26-3.29 (m, 2H), 2.87-2.91 (m, 2H), 1.84-1.90 (m, 6H).

34

EXAMPLE 18

Preparation of 6-{[(2-[1-[3-fluoro-6-(methyloxy)-4-quinolinyl]-4-hydroxy-4-piperidinyl]ethyl)amino]methyl}-2H-pyrido[3,2-b][1,4]oxazin-3(4H)-one

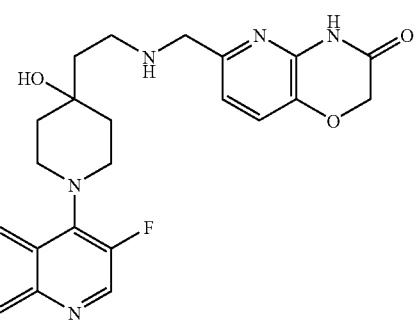

The title compound (71 mg, 26%) was prepared as a yellow solid according to Example 1, except substituting the following three reagents: 1,1-dimethylethyl [2-(4-hydroxy-4-piperidinyl)ethyl]carbamate (1.5 g, 6.15 mmol) [prepared according to Example 20] for 1,1-dimethylethyl [2-(1-piperazinyl)ethyl]carbamate, 4-bromo-3-fluoro-6-(methyloxy)quinoline (1.57 g, 6.15 mmol) for 8-bromo-7-fluoro-2-(methyloxy)-1,5-naphthyridine and 3-oxo-3,4-dihydro-2H-pyrido[3,2-b][1,4]oxazine-6-carbaldehyde (100 mg, 0.564 mmol) for 3-oxo-3,4-dihydro-2H-pyrido[3,2-b][1,4]thiazine-6-carbaldehyde: LCMS (ES) m/e 482 (M+H)$^+$; $^1$H NMR (400 MHz, CD$_3$OD) δ 8.47 (d, J=4.6 Hz, 1H), 7.87 (d, J=9.1 Hz, 1H), 7.39 (d, J=2.7 Hz, 1H), 7.33 (dd, J=2.7, 6.3 Hz, 1H), 7.28 (d, J=8.0 Hz, 1H), 6.99 (d, J=8.0 Hz, 1H), 4.65 (s, 2H), 3.96 (s, 3H), 3.81 (s, 3H), 3.55-3.61 (m, 2H), 3.26-3.29 (m, 2H), 2.88-2.91 (m, 2H), 1.80-1.93 (m, 6H).

EXAMPLE 19

Preparation of 6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one (a) hydroxy[1-(phenylmethyl)-4-piperidinyl]acetonitrile

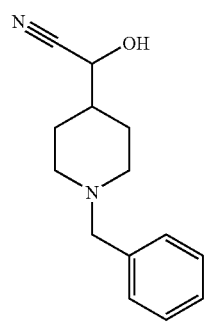

To a solution of 1-(phenylmethyl)-4-piperidinecarbaldehyde (2.35 g, 11.6 mmol)[prepared according to Alfaro-Lopez, J.; et al. *J. Med. Chem.* 1999, 42, 5359] in THF (160 mL) at 0° C. was added dropwise Et$_2$AlCN (25 mL, 1 M solution in toluene). After 1 h, the solution was partitioned between NaHCO$_3$(sat)-DCM. The aqueous phase was extracted several times with DCM and the combined organic fractions were dried (Na$_2$SO$_4$) and concentrated yielding the title compound as a yellow oil which was used directly without further purification: LCMS (ES) m/e 249 (M+H)$^+$.

(b) 2-amino-1-[1-(phenylmethyl)-4-piperidinyl]ethanol

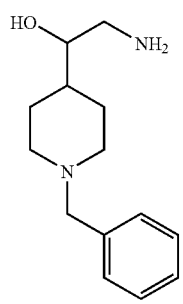

To a solution of LiAlH$_4$ (1.1 g, 28.7 mmol) in THF (25 mL) at 0° C. was added dropwise via addition funnel a solution of hydroxy[1-(phenylmethyl)-4-piperidinyl]acetonitrile (2.2 g, 9.56 mmol) in THF (25 mL). After 12 h at 25° C., the solution was carefully quenched by dropwise additional of sodium potassium tartrate and extracted several times with DCM. The combined organic fractions were dried (Na$_2$SO$_4$) and concentrated yielding the title compound as a yellow oil which was used without further purification: LCMS (ES) m/e 235 (M+H)$^+$.

(c) 1,1-dimethylethyl {2-hydroxy-2-[1-(phenylmethyl)-4-piperidinyl]ethyl}carbamate

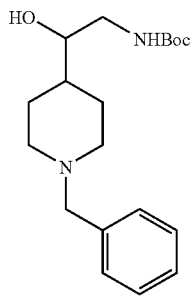

To a solution of 2-amino-1-[1-(phenylmethyl)-4-piperidinyl]ethanol (2.2 g, 9.4 mmol) in CH$_3$CN-THF (50 mL, 1:1) at 25° C. was added Boc$_2$O (2.4 mL, 11.2 mmol). After 0.5 h, the solution was concentrated and the residue purified via column chromatography (silica, 3-5% MeOH in DCM (1% NH$_4$OH)) yielding the title compound (2 g, 64%) as a yellow oil: LCMS (ES) m/e 335 (M+H)$^+$.

(d) 1,1-dimethylethyl [2-hydroxy-2-(4-piperidinyl)ethyl]carbamate

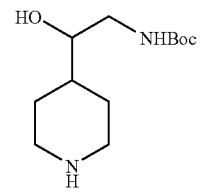

A solution of 1,1-dimethylethyl {2-hydroxy-2-[1-(phenylmethyl)-4-piperidinyl]ethyl}carbamate (2 g, 5.97 mmol) and Pd(OH)$_2$ (1.2 g, 60 wt %) in ETOH (30 mL) was hydrogenated at 60 psi using a Parr Shaker. After 12 h, the solution was filtered through Celite® and concentrated affording the title compound as a yellow oil which was used directly without further purification: LCMS (ES) m/e 245 (M+H)$^+$.

(e) 6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one

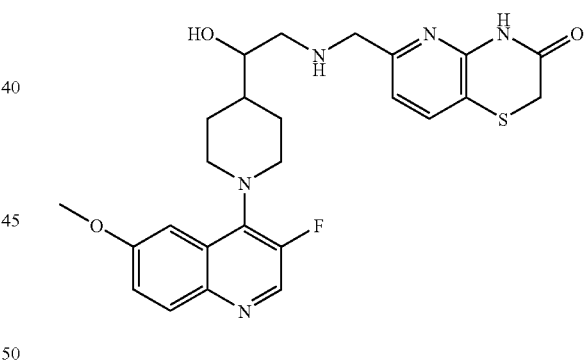

The title compound (10 mg, 16%) was prepared as a yellow solid according to Example 1, except substituting 1,1-dimethylethyl [2-hydroxy-2-(4-piperidinyl)ethyl]carbamate (1.5 g, 6.15 mmol) for 1,1-dimethylethyl [2-(1-piperazinyl)ethyl]carbamate as well as 4-bromo-3-fluoro-6-(methyloxy)quinoline (1.57 g, 6.15 mmol) for 8-bromo-7-fluoro-2-(methyloxy)-1,5-naphthyridine: LCMS (ES) m/e 498 (M+H)$^+$; $^1$H NMR (400 MHz, CD$_3$OD) δ 8.46 (d, J=4.5 Hz, 1H), 7.86 (d, J=9.1 Hz, 1H), 7.70 (d, J=7.7 Hz, 1H), 7.39 (d, J=2.7 Hz, 1H), 7.33 (dd, J=2.7, 6.3 Hz, 1H), 7.04 (d, J=7.7 Hz, 1H), 3.97 (s, 3H), 3.86 (AB quart., 2H), 3.60-3.65 (m, 1H), 3.53 (S, 2H), 3.49-3.53 (m, 1H), 3.24-3.26 (m, 2H), 2.80-2.84 (m, 1H), 2.68-2.71 (m, 1H), 1.99-2.01 (m, 1H), 1.67-1.70 (m, 5H).

| Example | Structure | Formula |
|---------|-----------|---------|
| 1 | 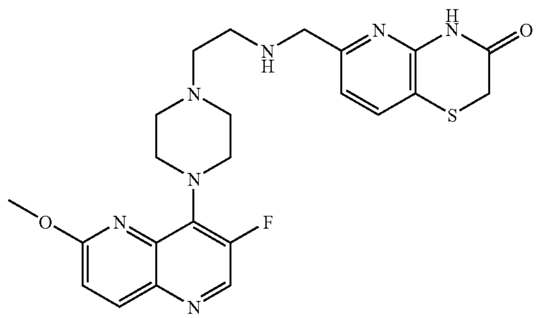 | 6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one |
| 2 | 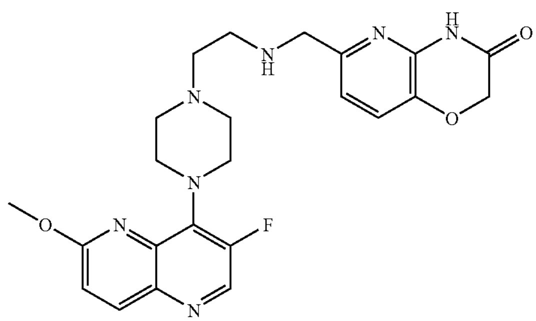 | 6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one |
| 3 | 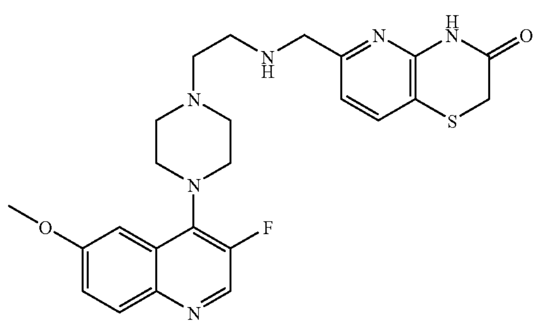 | 6-{[(2-{4-[3-fluoro-6-(methyloxy)-4-quinolinyl]-1-piperazinyl}ethyl)amino]methyl}-2H-pyrido[3,2-b][1,4]thiazin-3(4H)-one |
| 4 | 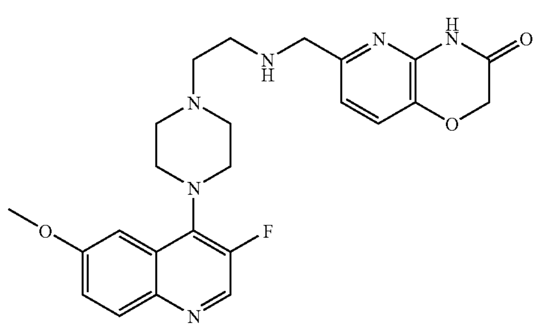 | 6-{[(2-{4-[3-fluoro-6-(methyloxy)-4-quinolinyl]-1-piperazinyl}ethyl)amino]methyl}-2H-pyrido[3,2-b][1,4]oxazin-3(4H)-one |

| Example | Structure | Formula |
|---|---|---|
| 5 | 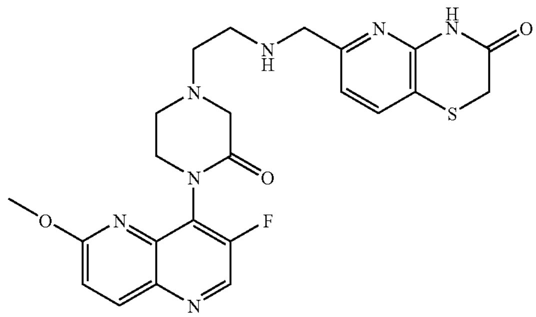 | 6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]thiazin-3(4H)-one |
| 6 | 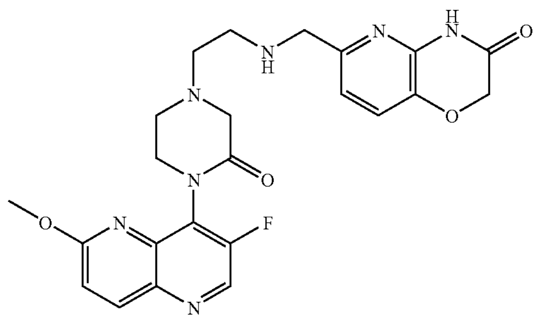 | 6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]oxazin-3(4H)-one |
| 7 | 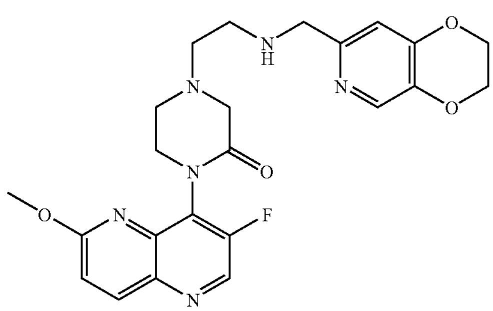 | 4-{2-[(2,3-dihydro[1,4]dioxino[2,3-c]pyridin-7-ylmethyl)amino]ethyl}-1-[3-fluoro-6-(methyloxy)-1,5-naphthyridin-4-yl]-2-piperazinone |
| 8 | 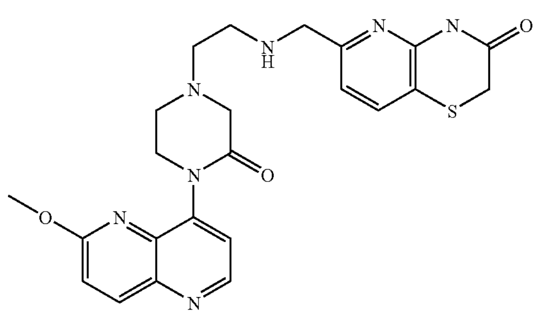 | 6-{[(2-{4-[6-(methyloxy)-1,5-naphthyridin-4-yl]-3-oxo-1-piperazinyl}ethyl)amino]methyl}-2H-pyrido[3,2-b][1,4]thiazin-3(4H)-one |
| 9 | 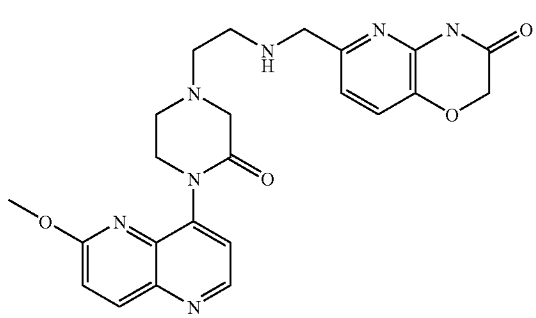 | 6-{[(2-{4-[6-(methyloxy)-1,5-naphthyridin-4-yl]-3-oxo-1-piperazinyl}ethyl)amino]methyl}-2H-pyrido[3,2-b][1,4]oxazin-3(4H)-one |

-continued

| Example | Structure | Formula |
|---|---|---|
| 10 | 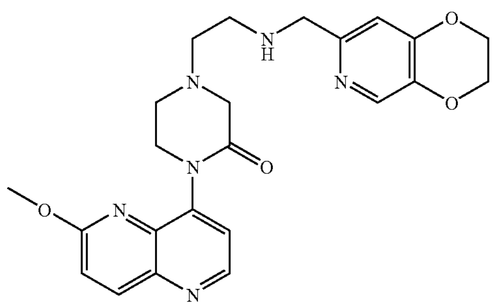 | 4-{2-[(2,3-dihydro[1,4]dioxino[2,3-c]pyridin-7-ylmethyl)amino]ethyl}-1-[6-(methyloxy)-1,5-naphthyridin-4-yl]-2-piperazinone |
| 11 | 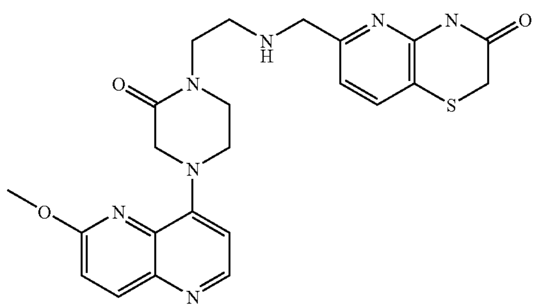 | 6-{[(2-{4-[6-(methyloxy)-1,5-naphthyridin-4-yl]-2-oxo-1-piperazinyl}ethyl)amino]methyl}-2H-pyrido[3,2-b][1,4]thiazin-3(4H)-one |
| 12 | 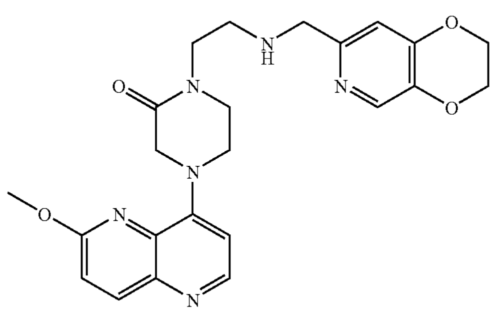 | 1-{2-[(2,3-dihydro[1,4]dioxino[2,3-c]pyridin-7-ylmethyl)amino]ethyl}-4-[6-(methyloxy)-1,5-naphthyridin-4-yl]-2-piperazinone |
| 13 | 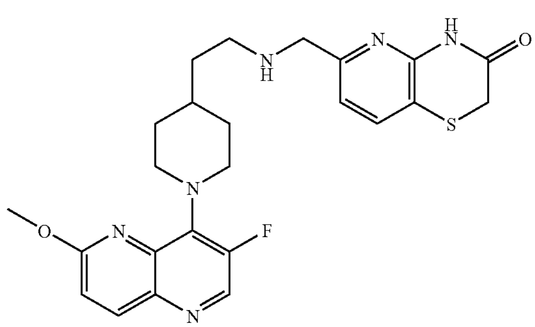 | 6-{[(2-{1-[3-fluoro-6-(methyloxy)-1,5-naphthyridin-4-yl]-4-piperidinyl}ethyl)amino]methyl}-2H-pyrido[3,2-b][1,4]thiazin-3(4H)-one |
| 14 | 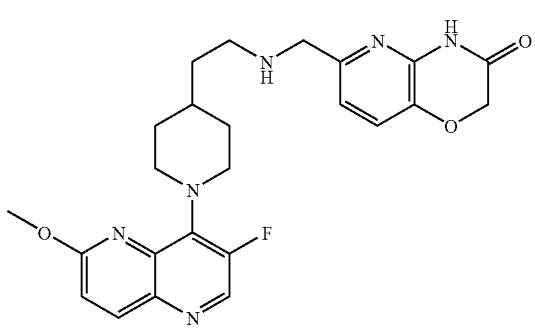 | 6-{[(2-{1-[3-fluoro-6-(methyloxy)-1,5-naphthyridin-4-yl]-4-piperidinyl}ethyl)amino]methyl}-2H-pyrido[3,2-b][1,4]oxazin-3(4H)-one |

-continued

| Example | Structure | Formula |
|---|---|---|
| 15 | 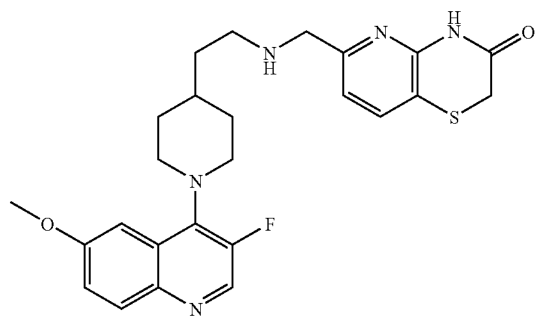 | 6-{[(2-{1-[3-fluoro-6-(methyloxy)-4-quinolinyl]-4-piperidinyl}ethyl)amino]methyl}-2H-pyrido[3,2-b][1,4]thiazin-3(4H)-one |
| 16 | 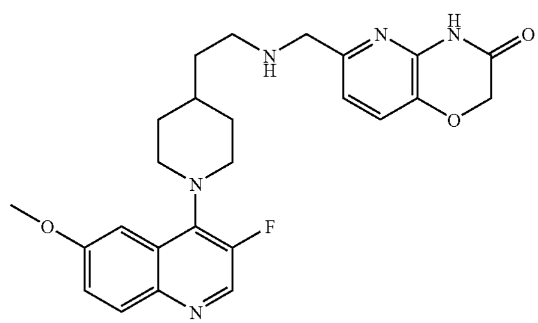 | 6-{[(2-{1-[3-fluoro-6-(methyloxy)-4-quinolinyl]-4-piperidinyl}ethyl)amino]methyl}-2H-pyrido[3,2-b][1,4]oxazin-3(4H)-one |
| 17 | 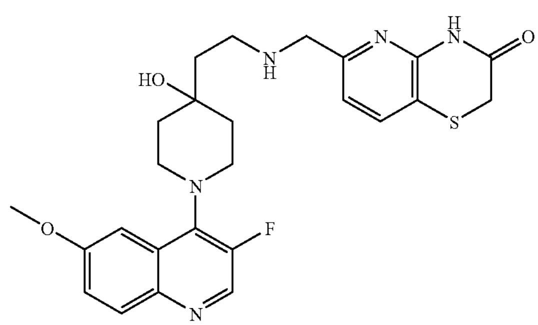 | 6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one |
| 18 | 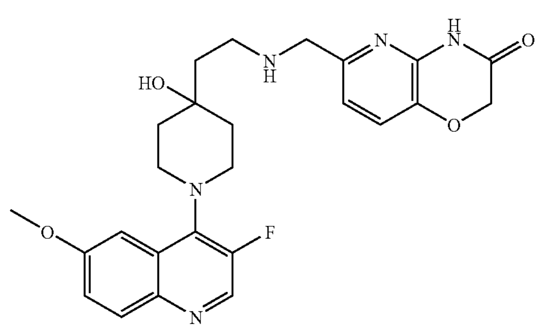 | 6-{[(2-{1-[3-fluoro-6-(methyloxy)-4-quinolinyl]-4-hydroxy-4-piperidinyl}ethyl)amino]methyl}-2H-pyrido[3,2-b][1,4]oxazin-3(4H)-one |

-continued

| Example | Structure | Formula |
|---|---|---|
| 19 | 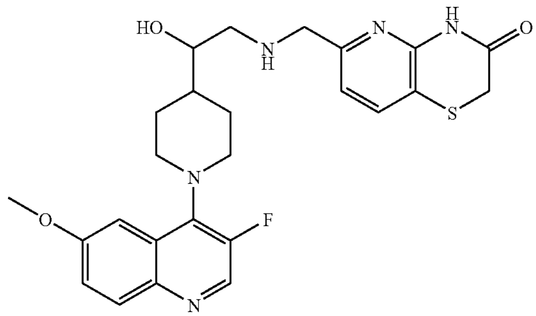 | 6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one |

EXAMPLE 20

Antimicrobial Activity Assay:

Whole-cell antimicrobial activity was determined by broth microdilution using the National Committee for Clinical Laboratory Standards (NCCLS) recommended procedure, Document M7-A6, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes*, and *Enterococcus faecalis*.

In addition, compounds were evaluated against a panel of Gram-negative strains including *Haemophilus influenzae, Moraxella catarrhalis* and *Escherichia coli*.

The minimum inhibitory concentration (MIC) was determined as the lowest concentration of compound that inhibited visible growth. A mirror reader was used to assist in determining the MIC endpoint.

One skilled in the art would consider any compound with a MIC of less than 20 mg/mL to be a potential lead compound. For instance, at least a substantial majority of the listed Examples (1 to 19), as identified in the present application, had a MIC ≦20 mg/ml against at least one of the organisms listed above.

What is claimed is:

1. A compound selected from:
   6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]thiazin-3(4H)-one;
   4-{2-[(2,3-dihydro[1,4]dioxino[2,3-c]pyridin-7-ylmethyl)amino]ethyl}-1-[3-fluoro-6-(methyloxy)-1,5-naphthyridin-4-yl]-2-piperazinone; and
   6-{[(2-{4-[3-fluoro-6-(methyloxy)-1,5-naphthyridin-4-yl]-3-oxo-1-piperazinyl}ethyl)amino]methyl}-2H-pyrido[3,2-b][1,4]oxazin-3(4H)-one;
   or a pharmaceutically acceptable salt thereof.

2. A pharmaceutical composition comprising a compound according to claim 1 and a pharmaceutically acceptable carrier.

3. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli*, or *Moraxella catarrhalis* which comprises administering to a mammal in need thereof an effective amount of a compound according to claim 1.

4. A compound selected from:
   6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one;
   6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one;
   6-{[(2-{1-[3-fluoro-6-(methyloxy)-1,5-naphthyridin-4-yl]-4-piperidinyl}ethyl)amino]methyl}-2H-pyrido[3,2-b][1,4]thiazin-3(4H)-one; and
   6-{[(2-{1-[3-fluoro-6-(methyloxy)-1,5-naphthyridin-4-yl]-4-piperidinyl}ethyl)amino]methyl}-2H-pyrido[3,2-b][1,4]oxazin-3(4H)-one;
   or a pharmaceutically acceptable salt thereof.

5. A compound according to claim 4, selected from:
   6-{[(2-{4-[3-fluoro-6-(methyloxy)-1,5-naphthyridin-4-yl]-1-piperazinyl}ethyl)amino]methyl}-2H-pyrido[3,2-b][1,4]thiazin-3(4H)-one; and
   6-{[(2-{4-[3-fluoro-6-(methyloxy)-1,5-naphthyridin-4-yl]-1-piperazinyl}ethyl)amino]methyl}-2H-pyrido[3,2-b][1,4]oxazin-3(4H)-one;
   or a pharmaceutically acceptable salt thereof.

6. A pharmaceutical composition comprising a compound according to claim 5 and a pharmaceutically acceptable carrier.

7. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli*, or *Moraxella catarrhalis* which comprises administering to a mammal in need thereof an effective amount of a compound according to claim 5.

8. A compound according to claim 4, selected from:
   6-{[(2-{1-[3-fluoro-6-(methyloxy)-1,5-naphthyridin-4-yl]-4-piperidinyl}ethyl)amino]methyl}-2H-pyrido[3,2-b][1,4]thiazin-3(4H)-one; and
   6-{[(2-{1-[3-fluoro-6-(methyloxy)-1,5-naphthyridin-4-yl]-4-piperidinyl}ethyl)amino]methyl}-2H-pyrido[3,2-b][1,4]oxazin-3(4H)-one;
   or a pharmaceutically acceptable salt thereof.

9. A pharmaceutical composition comprising a compound according to claim 8 and a pharmaceutically acceptable carrier.

10. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli, or Moraxella catarrhalis which comprises administering to a mammal in need thereof an effective amount of a compound according to claim 8.

11. A compound selected from:
6-{[(2-{4-[6-(methyloxy)-1,5-naphthyridin-4-yl]-3-oxo-1-piperazinyl}ethyl)amino]methyl}-2H-pyrido[3,2-b][1,4]oxazin-3(4H)-one;
6-{[(2-{4-[6-(methyloxy)-1,5-naphthyridin-4-yl]-3-oxo-1-piperazinyl}ethyl)amino]methyl}-2H-pyrido[3,2-b][1,4]thiazin-3(4H)-one;
4-{2-[(2,3-dihydro[1,4]dioxino[2,3-c]pyridin-7-ylmethyl)amino]ethyl}-1-[6-(methyloxy)-1,5-naphthyridin-4-yl]-2-piperazinone;
6-{[(2-{4-[6-(methyloxy)-1,5-naphthyridin-4-yl]-2-oxo-1-piperazinyl}ethyl)amino]methyl}-2H-pyrido[3,2-b][1,4]thiazin-3(4H)-one; and
1-{2-[(2,3-dihydro[1,4]dioxino[2,3-c]pyridin-7-ylmethyl)amino]ethyl}-4-[6-(methyloxy)-1,5-naphthyridin-4-yl]-2-piperazinone;
or a pharmaceutically acceptable salt thereof.

12. A pharmaceutical composition comprising a compound according to claim 11 and a pharmaceutically acceptable carrier.

13. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli,* or *Moraxella catarrhalis* which comprises administering to a mammal in need thereof an effective amount of a compound according to claim 11.

14. A compound selected from:
6-{[(2-{4-[3-fluoro-6-(methyloxy)-4-quinolinyl]-1-piperazinyl}ethyl)amino]methyl}-2H-pyrido[3,2-b][1,4]thiazin-3(4H)-one;
6-{[(2-{1-[3-fluoro-6-(methyloxy)-4-quinolinyl]-4-piperidinyl}ethyl)amino]methyl}-2H-pyrido[3,2-b][1,4]thiazin-3(4H)-one;
6-{[(2-{1-[3-fluoro-6-(methyloxy)-4-quinolinyl]-4-piperidinyl}ethyl)amino]methyl}-2H-pyrido[3,2-b][1,4]oxazin-3(4H)-one;
6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one;
6-{[(2-{1-[3-fluoro-6-(methyloxy)-4-quinolinyl]-4-hydroxy-4-piperidinyl}ethyl)amino]methyl}-2H-pyrido[3,2-b][1,4]oxazin-3(4H)-one; and
6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one;
or a pharmaceutically acceptable salt thereof.

15. A compound according to claim 14 which is 6-{[(2-{4-[3-fluoro-6-(methyloxy)-4-quinolinyl]-1-piperazinyl}ethyl)amino]methyl}-2H-pyrido[3,2-b][1,4]thiazin-3(4H)-one; or a pharmaceutically acceptable salt thereof.

16. A pharmaceutical composition comprising a compound according to claim 15 and a pharmaceutically acceptable carrier.

17. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli,* or *Moraxella catarrhalis* which comprises administering to a mammal in need thereof an effective amount of a compound according to claim 15.

18. A compound according to claim 14 selected from:
6-{[(2-{1-[3-fluoro-6-(methyloxy)-4-quinolinyl]-4-piperidinyl}ethyl)amino]methyl}-2H-pyrido[3,2-b][1,4]thiazin-3(4H)-one;
6-{[(2-{1-[3-fluoro-6-(methyloxy)-4-quinolinyl]-4-piperidinyl}ethyl)amino]methyl}-2H-pyrido[3,2-b][1,4]oxazin-3(4H)-one;
6-{[(2-{1-[3-fluoro-6-(methyloxy)-4-quinolinyl]-4-hydroxy-4-piperidinyl}ethyl)amino]methyl}-2H-pyrido[3,2-b][1,4]thiazin-3(4H)-one;
6-{[(2-{1-[3-fluoro-6-(methyloxy)-4-quinolinyl]-4-hydroxy-4-piperidinyl}ethyl)amino]methyl}-2H-pyrido[3,2-b][1,4]oxazin-3(4H)-one; and
6-{[(2-{1-[3-fluoro-6-(methyloxy)-4-quinolinyl]-4-piperidinyl}-2-hydroxyethyl)amino]methyl}-2H-pyrido[3,2-b][1,4]thiazin-3(4H)-one;
or a pharmaceutically acceptable salt thereof.

19. A pharmaceutical composition comprising a compound according to claim 18 and a pharmaceutically acceptable carrier.

20. A method of treating bacterial infections in mammals due to *Staphylococcus aureus, Staphylococcus epidermidis, Streptococcus pneumoniae, Streptococcus pyogenes, Enterococcus faecalis, Enterococcus faecium, Haemophilus influenzae, E. coli,* or *Moraxella catarrhalis* which comprises administering to a mammal in need thereof an effective amount of a compound according to claim 18.

* * * * *